(12) United States Patent
Zagury et al.

(10) Patent No.: US 8,975,399 B2
(45) Date of Patent: Mar. 10, 2015

(54) BENZENESULFON AMIDE-COMPOUND TREATMENT OF A PATHOLOGICAL CONDITION LINKED TO AN EXCESSIVE EFFECT OF TNF

(76) Inventors: Jean-Francois Zagury, Paris (FR); Matthieu Montes, Paris (FR); Hadley Mouhsine, Kremlin Bicetre (FR); Helene Guillemain, Conflans Sainte Honorine (FR)

( * ) Notice: Subject to any disclaimer, the term of this patent is extended or adjusted under 35 U.S.C. 154(b) by 0 days.

(21) Appl. No.: 13/811,144

(22) PCT Filed: Jul. 19, 2011

(86) PCT No.: PCT/FR2011/051742
§ 371 (c)(1),
(2), (4) Date: Jan. 18, 2013

(87) PCT Pub. No.: WO2012/017166
PCT Pub. Date: Feb. 9, 2012

(65) Prior Publication Data
US 2013/0123266 A1 May 16, 2013

Related U.S. Application Data

(60) Provisional application No. 61/443,132, filed on Feb. 15, 2011.

(30) Foreign Application Priority Data

Jul. 19, 2010 (FR) ..................................... 10 55867

(51) Int. Cl.
| | | |
|---|---|---|
| *A61K 45/06* | (2006.01) | |
| *A61K 31/343* | (2006.01) | |
| *A61K 31/495* | (2006.01) | |
| *A61K 31/502* | (2006.01) | |
| *A61K 31/18* | (2006.01) | |
| *A61K 31/352* | (2006.01) | |
| *A61K 31/403* | (2006.01) | |
| *C07C 311/21* | (2006.01) | |
| *C07C 311/29* | (2006.01) | |
| *C07D 207/38* | (2006.01) | |
| *C07D 207/48* | (2006.01) | |
| *C07D 295/185* | (2006.01) | |
| *C07D 295/215* | (2006.01) | |
| *C07D 295/26* | (2006.01) | |
| *C07D 307/79* | (2006.01) | |
| *C07D 307/91* | (2006.01) | |
| *C07D 307/92* | (2006.01) | |

(Continued)

(52) U.S. Cl.
CPC ............. *A61K 45/06* (2013.01); *A61K 2121/00* (2013.01); *A61K 31/18* (2013.01); *A61K 31/343* (2013.01); *A61K 31/352* (2013.01); *A61K 31/403* (2013.01); *A61K 31/495* (2013.01); *A61K 31/502* (2013.01); *C07C 311/21* (2013.01); *C07C 311/29* (2013.01); *C07C 2103/20* (2013.01); *C07D 207/38* (2013.01); *C07D 207/48* (2013.01); *C07D 295/185* (2013.01); *C07D 295/215* (2013.01); *C07D 295/26* (2013.01); *C07D 307/79* (2013.01); *C07D 307/91* (2013.01); *C07D 307/92* (2013.01); *C07D 309/38* (2013.01); *C07D 317/66* (2013.01); *C07D 319/18* (2013.01); *C07D 405/12* (2013.01); *C07D 237/34* (2013.01); *C07D 241/04* (2013.01)
USPC ................. 544/248; 514/252.12; 514/255.01; 514/330; 514/468

(58) Field of Classification Search
CPC .............. A61K 2121/00; A61K 45/06; A61K 310/343; A61K 31/495; A61K 31/502
USPC ............... 514/252.12, 330, 248, 468, 255.01; 544/386; 546/189; 549/461
See application file for complete search history.

(56) References Cited

U.S. PATENT DOCUMENTS

| | | |
|---|---|---|
| 6,294,539 B1 | 9/2001 | Boliang et al. |
| 2002/0120137 A1 | 8/2002 | Houze et al. |

(Continued)

FOREIGN PATENT DOCUMENTS

| | | |
|---|---|---|
| EP | 0758021 B1 | 2/1997 |
| WO | 9402465 A1 | 2/1994 |

(Continued)

OTHER PUBLICATIONS

Adams, et al., Quinone imides. XXXIX. Adducts of quinone monoimides and conversion of active methylene adducts to benzofurans, Journal of the American Chemical Society 78, 658-63 (1956).*

Al-Masoudi, Najim et al., "Nitroimidazoles Part 6. Synthesis, Structure and In Vitro Anti-HIV Activity of New 5-Substituted Piperazinyl-4-Nitroimidazole Derivatives", Antiviral Chemistry & Chemotherapy, vol. 18, No. 4, 2007, pp. 191-200.

(Continued)

*Primary Examiner* — Erich A Leeser
(74) *Attorney, Agent, or Firm* — Browdy and Neimark, PLLC

(57) ABSTRACT

A benzene sulphonamide compound of formula I

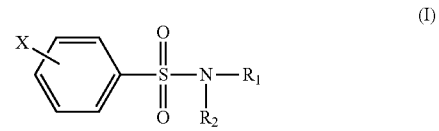

or one of its addition salts with pharmaceutically acceptable acids, for its use in a method for treating a pathology linked to an excessive effect of TNF-alpha and for its use in a method for treating the human or animal body as a direct inhibitor of TNF-alpha.

13 Claims, 10 Drawing Sheets

(51) Int. Cl.
*C07D 309/38* (2006.01)
*C07D 317/66* (2006.01)
*C07D 319/18* (2006.01)
*C07D 405/12* (2006.01)
*C07D 237/34* (2006.01)
*C07D 241/04* (2006.01)

(56) References Cited

U.S. PATENT DOCUMENTS

| | | | |
|---|---|---|---|
| 2009/0093415 A1 | 4/2009 | Yamano et al. | |
| 2009/0118292 A1 | 5/2009 | Deng et al. | |
| 2009/0163545 A1* | 6/2009 | Goldfarb | 514/312 |
| 2009/0186920 A1 | 7/2009 | Knust et al. | |

FOREIGN PATENT DOCUMENTS

| | | | | |
|---|---|---|---|---|
| WO | 9614317 A1 | 5/1996 | | |
| WO | 9816503 A2 | 4/1998 | | |
| WO | 9833768 A1 | 8/1998 | | |
| WO | 9926616 A1 | 6/1999 | | |
| WO | 0040576 A2 | 7/2000 | | |
| WO | 0147875 A1 | 7/2001 | | |
| WO | 03026651 A1 | 4/2003 | | |
| WO | 2004054974 A2 | 7/2004 | | |
| WO | 2004089415 A2 | 10/2004 | | |
| WO | 2004089470 A2 | 10/2004 | | |
| WO | 2007092681 A2 | 8/2007 | | |
| WO | 2007116374 A1 | 10/2007 | | |
| WO | 2007121124 A2 | 10/2007 | | |
| WO | 2009133294 A2 | 11/2009 | | |
| WO | WO 2009/133294 | * 11/2009 | | A61K 31/167 |
| WO | WO 2009/149192 | * 12/2009 | | A61K 31/275 |
| WO | 2010003023 A2 | 1/2010 | | |
| WO | 2010125831 A1 | 11/2010 | | |

OTHER PUBLICATIONS

Kumar Parai, Maloy et al., "Design, Synthesis, and Antimalarial Activity of Benzene and Isoquinoline, Sulfonamide Derivatives", Bioorganic & Medicinal Chemistry Letters, vol. 18, 2008, pp. 776-781.

Meng, Charles Q. et al., "Nitrobenzene Compounds Inhibit Expression of VCAM-1", Bioorganic & Medicinal Chemistry Letters, vol. 11, 2001, pp. 1823-1827.

Namba, Kensuke et al., "Design and Synthesis of Benzenesulfonanilides Active Against Methicillin-Resistent *Staphylococcus aureus* and Vancomycin-Resistent *Enterococcus*", Bioorganic & Medicinal Chemistry Letters, vol. 16, 2008, pp. 6131-6144.

* cited by examiner

BENZENESULFON AMIDE-COMPOUND TREATMENT OF A PATHOLOGICAL CONDITION LINKED TO AN EXCESSIVE EFFECT OF TNF

The present invention relates to sulphonated compounds for their use in a method for treating a pathology linked to an excessive effect of TNF.

Pharmacologically, the effects of TNF-alpha can be either beneficial and have to be reinforced, or excessive and it would be desirable to reduce them.

A certain number of pathologies linked to an excess of TNF-alpha (tumour necrosis factor) remain a problem. Mention may be made in particular of septic shock. TNF-alpha is also involved in Crohn's disease, heart failure and atherosclerosis. It also plays an important role in rheumatoid arthritis.

There are considered to be three ways of countering TNF: reducing its production, neutralizing it and blocking its targets.

Thalidomide reduces the production of TNF-alpha in vitro and in vivo. But, when taken by pregnant women, it causes a very large number of malformations. It is a teratogenic product. Apart from its teratogenic effect, prolonged administration of thalidomide is a cause of neuropathies. A steroidal anti-inflammatory, dexamethasone, also reduces the release of TNF.

The anti-TNF monoclonal antibodies bind to TNF, neutralize it and block its action. Patients treated with infliximab for the treatment of rheumatoid arthritis, Crohn's disease and ankylosing spondylitis can be subject to reactions of the immune system against infleximab. Adalimumab is an anti-TNF-alpha humanized monoclonal antibody which reduces this type of reaction. Soluble TNF receptors can also bind to TNF and prevent it from acting. Etanercept is used in the treatment of rheumatoid arthritis and ankylosing spondylitis. But, like the monoclonal antibodies, the soluble anti-TNF receptors can be associated with undesirable effects such as infections (tuberculosis and others) or the appearance of certain cancers.

In summary, these approaches have considerably improved the treatment of the chronic inflammatory diseases and show that the inhibition of TNF-alpha is an important means of treating these diseases. However, these products have serious drawbacks: they require the sub-cutaneous or intravenous injection of the product every two to four weeks and they can induce rare (1%) but serious side effects (tuberculosis, lymphomas).

This is why research is continuing into small molecules intended to combat the harmful effects of TNF-alpha, as they have several advantages: 1. they can be absorbed by oral route and as a result allow better compliance with the treatment by the patient and better penetration of the tissues, 2. They present less or no risk of undesirable immunogenicity, 3. The treatment can be stopped and the product disappears immediately in the event of undesirable side effects.

Moreover, sulphonated compounds of formula I are well known,

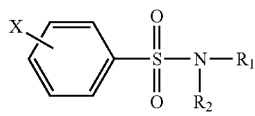
(I)

in which

R1 represents
- Φ a —CHR4-CO—R3 group, in which
  R4 represents a hydrogen atom or a C1-C5 alkyl and
  R3 represents an organic group, said organic group comprising 11 or more than 11 atoms other than H and containing from 6 to 30 carbon atoms including one or more rings or heterocycles, saturated or unsaturated, fused or not, optionally substituted by one or more substituents, preferably 1, 2 or 3, in particular 1 or 2 substituents chosen from the C1-C5 alkyl, C1-C5 alkenyl, halogeno, C3-C8 cycloalkyl, C1-C5 alkoxy, C1-C5 alkylthio, C1-C5 alkylsulphonyl, acyl, hydroxy, NH2, nitro, C1-C5 alkylamino, di(C1-C5 alkyl)amino, acylamino radicals, said organic group not being linked to the carboxyl by an —NH—CH2— group or by an —NH—CH-alk-group where alk represents an alkyl radical with 1 to 5 carbon atoms, said organic group not comprising a

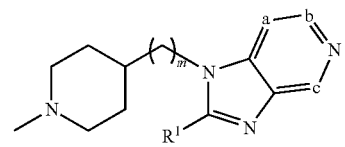

group in which m represents 0, 1 or 2, a, b and c represent CR, where each R represents independently a hydrogen or a C1-C4 alkyl, R1 represents a C1-C4 alkyl or a C3-C7 cycloalkyl, said organic group not comprising a —CO—NHOH group, said organic group not representing a

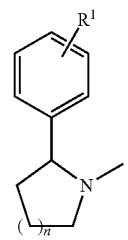

group in which n=1 or 2 and R1 represents H, halogen, CN, lower alkyl or alkoxy, optionally substituted by a halogen,
- Φ a benzofuran group, preferably 5-benzofuran or naphthofuran, preferably 5-naphthofuran optionally substituted by one or more substituents, preferably 1, 2 or 3, in particular 1 or 2 substituents chosen from the C1-C5 alkyl, C1-C5 alkenyl, halogeno, C3-C8 cycloalkyl, C1-C5 alkoxy, C1-C5 alkylthio, C1-C5 alkylsulphonyl, acyl, hydroxy, NH2, nitro, C1-C6 alkylamino, di(C1-C6 alkyl)amino, acylamino radicals,
- Φ a hydrogen atom,
- Φ a group chosen from

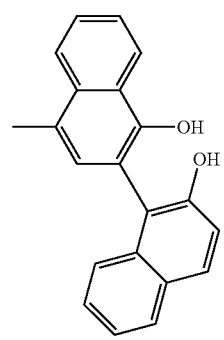

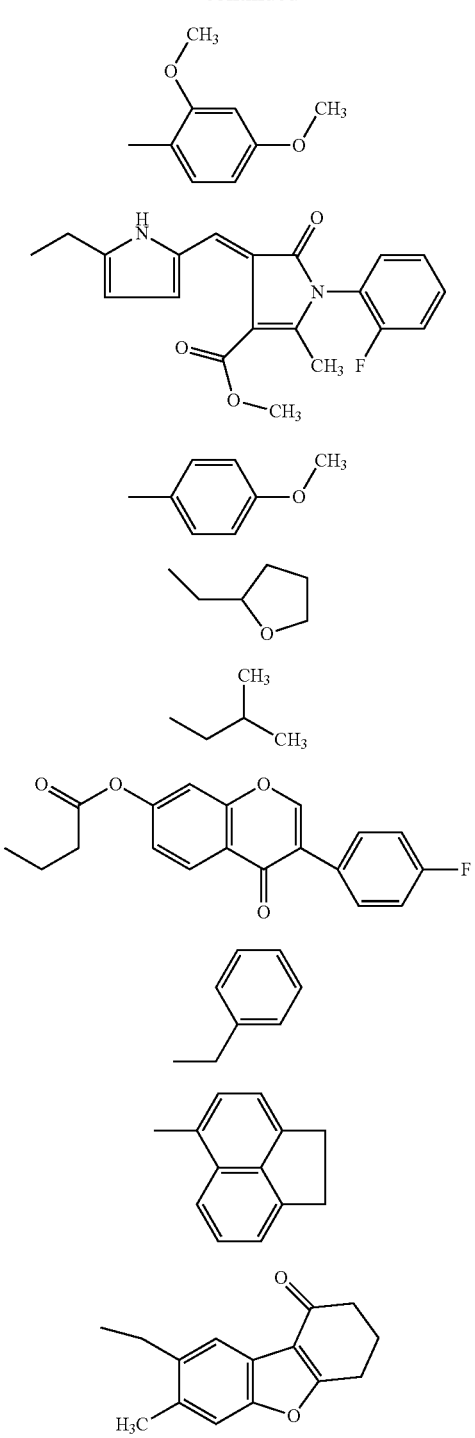

R2 represents
- Φ a phenyl or C4-C7 cycloalkyl group optionally substituted by one or more substituents, preferably 1, 2 or 3, in particular 1 or 2 substituents chosen from the C1-C5 alkyl, C1-C5 alkenyl, halogeno, C3-C8 cycloalkyl, C1-C5 alkoxy, C1-C5alkylthio, C1-C5alkylsulphonyl, acyl radicals except for —CONHOH, hydroxy, NH2, nitro, C1-C6 alkylamino, di(C1-C6 alkyl)amino radicals, two substitutents in meta position relative to one another being able to form a ring, said group being directly linked to the nitrogen, or linked by a —(CH$_2$)$_n$— group where n=1, 2 or 3, preferably 1 or 2,
- Φ a hydrogen atom, it being understood that R1 and R2 cannot represent hydrogen at the same time, X represent a hydrogen atom or one or more substituents, preferably 1, 2 or 3, in particular 1 or 2 substituents chosen from the C1-C5 alkyl, C1-C5 alkoxy, C1-C5 alkenyl, halogeno, C3-C8 cycloalkyl, C1-C5 alkylthio, C1-C5 alkylsulphonyl, acyl, hydroxy, NH2, nitro, C1-C6 alkylamino, di(C1-C6 alkyl) amino, acylamino radicals, it being understood that X is not a 3,4-dialkoxy or a 3,4-dialkylthio, as well as the compound of formula I below for which R2=H:

the compound for which

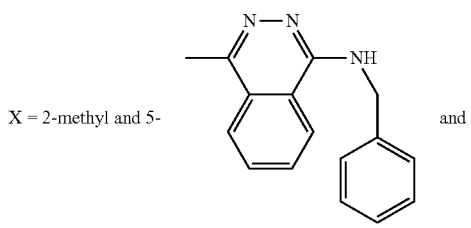

X = 2-methyl and 5-    and

R1 = 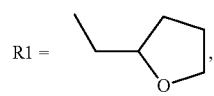, the compound for which

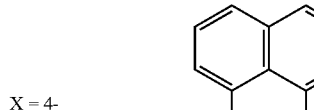

the compound for which

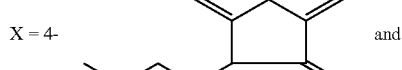

the compound for which

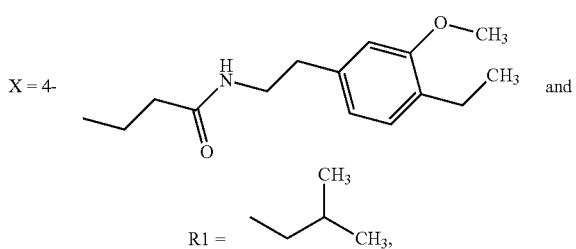

the compound for which

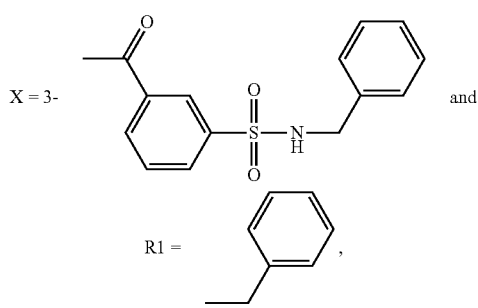

the compound for which

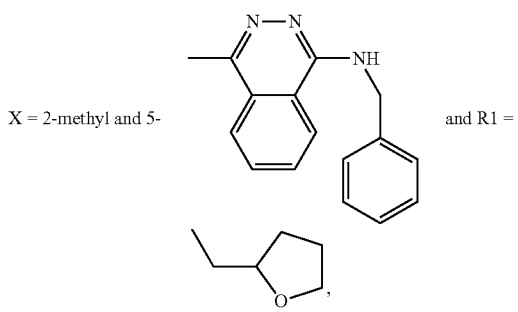

it being understood that
- if R1=H and X is a 3-nitro, 4-chloro, R2 is not a methyl, ethyl or benzyl radical,
- if R1=H, R2 is not a 3,4-dimethoxy phenethyl,
- if X=H or alkyl optionally substituted in position 4, R2 is not an optionally substituted phenyl radical, as well as 3-(3-phenoxyphenyl)-2-(phenylsulphonyl)-N-(3-pyridinylmethyl) acrylamide, as well as their addition salts with pharmaceutically acceptable acids.

These sulphonated compounds are known and commercially available in particular from ChemBridge Corporation (www.chembridge.com). These sulphonated compounds can be prepared according to well-known methods. Mention may be made in particular of Lemaire et al., Eur J Org Chem 13, 2840:2847 (2004), and Adams, R and Whitaker, L, J Am Chem Soc (1953),78:658-663 showing how different benzinic acids or derivatives of active methylenes placed in the presence of p-quinonemonobenzenesulphonimide or of naphthoquinonemonobenzene-sulphonimides in acid medium, form benzofuran or naphthofuran derivatives respectively.

WO 99/26616 A1, WO 94/02465 A1, Meng Charles Q et al.: "Nitrobenzene compounds inhibit expression of VCAM-1", Bioorganic & Medicinal Chemistry Letters, Pergamon, Elsevier Science, GB, vol. 11, no. 14, 23 Jul. 2001, Kumar Parai et al.: "Design, synthesis and antimalarial activity of benzene and isoquinoline sulfonamide derivatives, Bioorganic & Medicinal Chemistry Letters, Pergamon, Elsevier Science, GB, vol. 18, no. 2, 17 Nov. 2007 (2007-Nov.-17), pages 776-781, Namba K et al.: Design and synthesis of benzenesulphonanilides active against methicillin-resistant *Staphylococcus aureus* and vancomycin-resistant *Enterococcus*, Bioorganic & Medicinal Chemistry, Pergamon, G B, vol. 16, no. 11, 1 Jun. 2008 (2008-Jun.-1), pages 6131-6144, WO 2008/076918 A2, US 2009/118292 A1, WO 98/33768 A1, WO 98/16503 A2, WO 03/026651 A1, U.S. Pat. No. 6,294, 539 B1, WO 96/14317 A1, US 2009/186920 A1, WO 01/47875 A1, WO 2007/116374 A1, US 2002/120137 A1, US 2009/093415 A1, WO 2010/003023 A2, WO 02/32864 A1 and WO 2010/125831 A1 also describe compounds of formula I or of similar structure.

In the present application, the expression "C1-C5 alkyl" denotes a linear or branched alkyl group with 1 to 5 carbon atoms inclusive, such as the methyl, ethyl, propyl, 1-propyl, 2-propyl, 1-butyl, 2-butyl, 2-methyl-2-propyl and 2-methyl-1-propyl, preferably methyl or ethyl groups, Similarly, "C2-C5 alkenyl" and "C2-C5 alkynyl" denote such groups having 2 to 5 carbon atoms inclusive respectively.

Halogeno means fluoro, chloro, bromo or iodo, preferably bromo or chloro, particularly the latter.

The expression "C3-C8 cycloalkyl" denotes a monocyclic or bicyclic carbon ring with 3 to 8 carbon atoms, comprising, but without being limited thereto, the cyclopropyl, cyclobutyl, cyclopentyl, cyclohexyl, cycloheptyl and cyclooctyl groups.

The expressions C1-C5 alkoxy, C1-C5 alkylthio and C1-C5 alkylsulphonyl, denote such groups in which the C1-C5 alkyl group is as defined above.

The term "acyl" means —CO-alkyl where the alkyl group is a C1-C5 alkyl as defined above.

"Amino" means NH2.

"C1-C5 alkylamino" means —NH-alkyl and "di(C1-C5 alkyl)amino" means —N=(alkyl)$_2$ where the alkyl group is a C1-C5 alkyl as defined above.

"Acylamino" means —NH-acyl where acyl has the above definition.

The organic group comprising 11 or more than 11 atoms other than H and containing from 6 to 30 carbon atoms including one or more rings or heterocycles, saturated or unsaturated, fused or not, can comprise as rings or heterocycles, phenyl groups, mono- or bicyclic heterocyclic groups containing at least one N, S or O atom, such as the furyl, pyrrolyl, thienyl, oxazolyl, isoxazolyl, thiazolyl, isothiazolyl, imidazolyl, pyridyl, pyrimidyl, tetrazolyl, benzofuranyl, benzothienyl, benzimidazolyl, indolyl groups. Preferred heterocycles are monocyclic. The thienyl and piperidinyl groups, as well as piperazinyl are especially preferred.

Organic groups comprising 11 or more than 11 atoms other than H and containing from 6 to 30 carbon atoms including one or more preferred rings or heterocycles, saturated or unsaturated, fused or not are phenyl, benzyl, phenethyl, piperazinyl, phenylpiperazinyl, phenylamino, benzylamino, benzo(c)piperidinyl groups. Their preferred substituents are C1-C5 alkyl, C1-C5 alkenyl, halogeno and C1-C5 alkoxy groups.

Examples of addition salts of organic acids according to the invention are those formed with maleic, fumaric, benzoic, ascorbic, succinic, oxalic, bis-methylenesalicylic, methanesulphonic, ethanedisulphonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulphonic and theophylline-acetic acids. Examples of addition salts of inorganic acids according to the invention are those formed with hydrochloric, hydrobromic, sulphuric, sulphamic, phosphoric and nitric acids. The addition salts of acids of the invention are preferably pharmaceutically acceptable salts formed with non-toxic acids.

Their toxicological properties are also well known.

The Applicant has surprisingly discovered that the sulphonated compounds of formula I above possess very useful original pharmacological properties. They are in particular endowed with remarkable direct anti-TNF-alpha properties, acting on the detrimerization of cytokine, converting it to inactive dimer. As a reminder, TNF-alpha is pharmacologically active in trimer form. To the Applicant's knowledge, this technical effect has never been described for the sulphonated compounds above.

These properties are illustrated below in the experimental part. They justify the use of the sulphonated compounds of formula I above and the sulphonated compound 3-(3-phenoxyphenyl)-2-(phenylsulphonyl)-N-(3-pyridinylmethyl) acrylamide or one of their addition salts with pharmaceutically acceptable acids, for their use in a method for treating a non-cancer pathology linked to an excessive effect of TNF-alpha chosen from the inflammatory diseases of the intestine, inflammation, chronic inflammatory diseases, rheumatoid arthritis, juvenile rheumatoid arthritis, psoriatic arthritis, arthrosis, refractory rheumatoid arthritis, non-rheumatoid chronic arthritis, bone resorption/osteoporosis, Crohn's disease, haemorrhagic rectocolitis, septic shock, endotoxin shock, atherosclerosis, ischaemia-reperfusion lesions, coronary heart disease, vasculitis, amydoloidosis, multiple sclerosis, septicaemia, chronic recurrent uveitis, hepatitis C virus, malaria, ulcerative colitis, cachexia, psoriasis, endometriosis, Behçet's disease, Wegener's granulomatosis, meningitis, AIDS, HIV infections, auto-immune diseases, immunodeficiency, common variable immunodeficiency (CVID), chronic graft-versus-host diseases, trauma and graft rejections, respiratory distress syndrome, pulmonary fibrosis, diabetes, juvenile diabetes, ankylosing spondylitis, and skin disorders due to delayed-type hypersensitivity reactions, Alzheimer's disease, disseminated lupus erythematosus, and allergic asthma and more generally the inflammatory diseases for which the anti-TNF biotherapies (monoclonal antibodies, soluble receptors) are effective.

They justify the use of the sulphonated compounds above as well as of their addition salts with pharmaceutically acceptable acids for producing a medicament intended for the treatment of a pathology linked to an excessive effect of TNF-alpha, or for the production of an anti-TNF-alpha agent in particular a direct anti-TNF-alpha agent.

This is why a subject of the present invention is also the sulphonated compounds described above for their use in a method for treating a pathology linked to an excessive effect of TNF-alpha, in particular by direct action, acting on the detrimerization of TNF-alpha.

Among the sulphonated compounds described above the sulphonated compounds of formula I in particular are retained, for which
R1 represents a —CHR4-CO—R3 group, in which
R4 represents a hydrogen atom or a C1-C5 alkyl and
R3 has the meanings already indicated and in particular represents an organic group comprising 11 or more than 11 atoms other than H and containing from 6 to 20 carbon atoms, particularly a

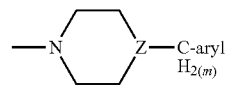

group in which m has the value 0, 1 or 2 and preferably the value 0 or 1, Z has the meaning N or CH, and Ar represents an aryl radical, preferably a phenyl radical, the aryl radical being able to be substituted by one or more radicals having the meaning already indicated, but the aryl radical is preferably not substituted or is substituted by 1 or 2 halogens or alkoxy, and
R2 and X have the meaning already indicated, X being preferably H, halo, alkoxy or alkyl.

Among the sulphonated compounds described above in particular the sulphonated compounds of formula I are also retained, for which
R1 represents a —CHR4-CO—R3 group, in which R3 and R4 have the meaning already indicated,
R2 represents an optionally substituted phenyl group, said phenyl group being directly linked to the nitrogen, or linked by a —(CH$_2$)— group, and X has the meaning already indicated, preferably H, halo, alkoxy or alkyl, as well as their addition salts with pharmaceutically acceptable acids.

Among the sulphonated compounds described above in particular the sulphonated compounds of formula I are also retained for which
R1 represents a —CHR4-CO—R3 group, in which R4 represents a hydrogen atom or a C1-C5 alkyl and R3 represents an organic group comprising 11 or more than 11 atoms other than H and containing from 6 to 20 carbon atoms, particularly a

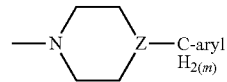

group in which m has the value 0, 1 or 2 and preferably the value 0 or 1, Z has the meaning N or CH, and Ar represents an aryl radical, preferably a phenyl radical. The aryl radical can be substituted by one or more radicals having the meaning already indicated, but the aryl radical is preferably not substituted or is substituted by 1 or 2 halogens or alkoxy. R2 represents an optionally substituted phenyl group, said phenyl group being directly linked to the nitrogen, or linked by a —(CH$_2$)— group, and X has the meaning already indicated, preferably H, halo, alkoxy or alkyl, as well as their addition salts with pharmaceutically acceptable acids.

Among the sulphonated compounds described above, in particular the sulphonated compounds of formula I are also retained, for which
R1 represents a —CHR4—CO—R3 group where R3 represents a

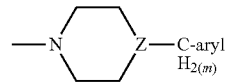

group in which m has the value 0, 1 or 2 and preferably the value 0 or 1, Z has the meaning N or CH, and Ar represents an aryl radical, preferably an optionally substituted phenyl radical, and R2 and X have the meaning indicated in the previous paragraph, as well as their addition salts with pharmaceutically acceptable acids.

Among the sulphonated compounds described above the sulphonated compounds of formula I are also retained, for which R2 =H as well as their addition salts with pharmaceutically acceptable acids.

The sulphonated compounds of formula I are also retained, for which R2=H, R1 represents
- a benzofuran group, preferably 5-benzofuran or naphthofuran, preferably 5-naphthofuran optionally substituted by one or more substituents, preferably 1, 2 or 3, in particular 1 or 2 substituents chosen from the C1-C5 alkyl, preferably methyl or ethyl, C1-C5 alkenyl, halogeno, C3-C8 cycloalkyl, C1-C5 alkoxy, preferably methoxy or ethoxy, C1-C5 alkylthio, C1-C5 alkylsulphonyl, acyl, amino, C1-C6 alkylamino, di(C1-C6 alkyl)amino, acylamino radicals, or
- a group chosen from the above groups a, b, c, d, e, f, g, h, i and j, and X has the meaning already indicated, preferably H, halo, alkoxy or alkyl,
as well as their addition salts with pharmaceutically acceptable acids More particularly the sulphonated compounds of formula I above are also retained, for which R1 represents a —CHR4—CO—R3 group, in which R3 and R4 have the meaning already indicated, R2 represents a phenyl or optionally substituted C4-C7 cycloalkyl group, and X has the meaning already indicated, preferably H, halo, alkoxy or alkyl, as well as their addition salts with pharmaceutically acceptable acids.

Among the sulphonated compounds of the invention, more particular mention may be made of the products mentioned in the experiments, in particular those for which the 10 μM inhibition percentage is greater than 50%, particularly greater than 55%, more particularly greater than 60%, quite particularly greater than 70% as well as their addition salts with pharmaceutically acceptable acids.

The following products, as well as their addition salts with pharmaceutically acceptable acids may more particularly be mentioned:
1—N-(3-acetyl-2-methylnaphthho[1,2-b]furan-5-yl)-4-ethoxybenzene sulphonamide (Z1)
2—N-(3-acetyl-2,6-dimethyl-1-benzofuran-5-yl)-4-methoxybenzene sulphonamide
3—N-benzyl-4-methoxy-N-{2-[4-(2-methoxyphenyl)-1-piperazinyl]-2-oxoethyl}-3-methylbenzenesulphonamide (Z2=32)
4—methyl 1-(2-fluorophenyl)-2-methyl-5-oxo-4-[(5-{[(phenylsulphonyl)amino]methyl}-2-furyl)methylene]-4,5-dihydro-1H-pyrrole-3-carboxylate
5—methyl 5-{[(4-methoxyphenyl)sulphonyl]amino}-2-methyl-1-benzofuran-3-carboxylate
6—N-(1',2-dihydroxy-1.2'-binaphthhalen-4'-yl)-4-methoxy-benzene-sulphonamide
7—N~2~-(3-chlorobenzyl)-N~1~-(2,4-dimethoxyphenyl)-N~2~-[(4-methylphenyl)sulphonyl]glycinamide
8—3-(4-fluorophenyl)-4-oxo-4H-chromen-7-ylN-[(4-methylphenyl)sulphonyl]-beta-alaninate
9—methyl 2-methyl-5-{[(4-methylphenyl)sulphonyl]amino}-1-benzofuran-3-carboxylate
10—5-[4-(benzylamino)-1-phthalazinyl]-2-methyl-N-(tetrahydro-2-furanylmethyl)benzenesulphonamide
11—N-(1,2-dihydro-5-acenaphthhylenyl)-2.4,6-trimethyl-benzenesulphonamide
12—N~1~-(3-acetylphenyl)-N-~2~-(2,5-dimethoxyphenyl)-N-~2~-[(4-methylphenyl)sulphonyl]glycinamide, as well as
13—N-[2-(4-benzyl-1-piperazinyl)-2-oxoethyl]-N-(3-chlorophenyl)-4-methyl benzenesulphonamide (Z4=65)
14—N-benzyl-4-chloro-N-{2-[4-(2-methoxyphenyl)-1-piperazinyl]-2-oxoethyl}benzenesulphonamide (Z5=66)
15—N-benzyl-4-bromo-N-{2-[4-(2-methoxyphenyl)-1-piperazinyl]-2-oxoethyl}benzenesulphonamide (Z6=67)
16—N-[2-(4-benzyl-1-piperazinyl)-2-oxoethyl]-N-(4-chlorophenyl)-4-methyl benzenesulphonamide (Z7=68)
17—N-benzyl-4-methoxy-N-{2-[4-(2-methoxyphenyl)-1-piperazinyl]-2-oxoethyl}-3-methylbenzenesulphonamide
18—N-benzyl-4-methyl-N-[2-oxo-2-(4-phenyl-1-piperazinyl)pethyl]benzenesulphonamide (Z8=69)
19—N-{2-[4-(2-fluorophenyl)-1-piperazinyl]-2-oxoethyl}-N-(4-methylbenzyl) benzenesulphonamide (Z3=70)
20—4-chloro-N-(4-fluorobenzyl)-N-{2-[4-(2-methoxyphenyl)-1-piperazinyl]-2-oxoethyl}benzenesulphonamide
21—N-[2-(4-benzyl-1-piperazinyl)-2-oxoethyl]-N-(3,4-dimethylphenyl)-4-methylbenzenesulphonamide (Z9=72)
22—N-[2-(4-benzyl-1-piperazinyl)-2-oxoethyl]-N-(3-chloro-2-methylphenyl)benzenesulphonamide (Z10=73)
23—4-chloro-N-(3,4-dichlorobenzyl)-N-[2-(4-methyl-1-piperidinyl)-2-oxoethyl]benzenesulphonamide
24—N-benzyl-4-fluoro-N-{2-[4-(2-methoxyphenyl)-1-piperazinyl]-2-oxoethyl}benzenesulphonamide
25—N-[2-(4-benzyl-1-piperazinyl)-2-oxoethyl]-N-(3,5-dimethylphenyl)-4-methylbenzenesulphonamide
26—N-benzyl-N-{2-[4-(2-fluorophenyl)-1-piperazinyl]-2-oxoethyl}-4-methoxybenzenesulphonamide
27—N-[2-(3,4-dihydro-2(1H)-isoquinolinyl)-2-oxoethyl]-N-(3,5-dimethylphenyl)-3,4-d imethoxybenzenesulphonamide
28—3,4-dimethoxy-N-(4-methylphenyl)-N-[2-oxo-2-(4-phenyl-1-piperazinyl)ethyl]benzenesulphonamide
29—N-{2-[4-(4-fluorophenyl)-1-piperazinyl]-2-oxoethyl}-N-(4-methylbenzyl)benzenesulphonamide
30—N-[2-(4-benzyl-1-piperidinyl)-2-oxoethyl]-N-(4-fluorophenyl)-4-methylbenzenesulphonamide
31—N-[2-(4-benzyl-1-piperazinyl)-2-oxoethyl]-4-methyl-N-(2-methylphenyl)benzenesulphonamide
32—N-benzyl-N-{2-[4-(4-fluorophenyl)-1-piperazinyl]-2-oxoethyl}-4-methylbenzenesulphonamide
33—N-(3-chlorophenyl)-4-methyl-N-[2-oxo-2-(4-phenyl-1-piperazinyl)ethyl]benzenesulphonamide
34—N-benzyl-N-{2-[4-(4-fluorophenyl)-1-piperazinyl]-2-oxoethyl}-3,4-dimethoxybenzenesulphonamide
35—N-{2-[4-(diphenylmethyl)-1-piperazinyl]-2-oxoethyl}-N,4-dimethyl benzenesulphonamide
36—N-(3-nitrophenyl)-N-[2-oxo-2-(4-phenyl-1-piperazinyl)ethyl]benzenesulphonamide.

More particular mention may also be made of the products bearing numbers 1, 2, 13, 14, 15, 16, 18, 19, 21 and 22, and quite particularly 13, 14, 16 and 21, as well as their addition salts with pharmaceutically acceptable acids.

However, compounds not according to formula I as defined above and not included within the scope of the claimed products are presented for comparison only.

The sulphonated compounds according to the present invention have direct anti-TNF-alpha properties by acting on the detrimerization of cytokine, converting it to inactive dimer. Thus, they can be used jointly with compounds having anti-TNF-alpha properties of a different nature such as for example compounds inhibiting the production of TNF-alpha, such as compounds active on the production of TNF by the monocytes, or compounds inhibiting the production of the pro-inflammatory cytokines including TNF. Thus, a subject of the present invention is also a pharmaceutical composition characterized in that it contains, as active ingredient, a direct anti-TNF-alpha sulphonated compound as defined above, a compound having anti-TNF-alpha properties of a different kind, as well as one or more pharmaceutically acceptable excipients.

The sulphonated compounds according to the present invention are used in both the curative and preventive treatment of the non-cancerous diseases known to be linked to the overproduction of TNF-alpha. The sulphonated compounds according to the present invention are used for example in both the curative and preventive treatment of the chronic inflammatory diseases known to be linked to the overproduction of TNF-alpha such as: the inflammatory diseases of the intestine, inflammations, chronic inflammatory diseases, rheumatoid arthritis, juvenile rheumatoid arthritis, psoriatic arthritis, arthrosis, refractory rheumatoid arthritis, non-rheumatoid chronic arthritis, bone resorption/osteoporosis, Crohn's disease, haemorrhagic rectocolitis, septic shock, endotoxin shock, atherosclerosis, ischaemia-reperfusion lesions, coronary heart disease, vasculitis, amydoloidosis, multiple sclerosis, septicaemia, chronic recurrent uveitis, hepatitis C virus, malaria, ulcerative colitis, cachexia, psoriasis, endometriosis, Behçet's disease, Wegener's granulomatosis, meningitis, AIDS, HIV infections, auto-immune diseases, immunodeficiency, common variable immunodeficiency (CVID), chronic graft-versus-host diseases, trauma and graft rejections, respiratory distress syndrome, pulmonary fibrosis, diabetes, juvenile diabetes, ankylosing spondylitis, and skin disorders due to delayed-type hypersensitivity reactions, Alzheimer's disease, disseminated lupus erythematosus, and allergic asthma and more generally the inflammatory diseases for which the anti-TNF biotherapies (monoclonal antibodies, soluble receptors) are effective.

The sulphonated compounds according to the present invention are used particularly in the treatment of the following diseases: inflammatory diseases of the intestine, rheumatoid arthritis, juvenile rheumatoid arthritis, psoriatic arthritis, refractory rheumatoid arthritis, haemorrhagic rectocolitis, Crohn's disease, septic shock, multiple sclerosis, chronic recurrent uveitis, cachexia, psoriasis, auto-immune diseases, immunodeficiency, ankylosing spondylitis, disseminated lupus erythematosus, and allergic asthma.

The usual dose, which can be varied according to the patient treated and the condition in question, can be, for example, from 10 mg to 10,000 mg, preferably from 50 mg to 5000 mg, or even from 200 mg to 3000 mg a day by oral route in humans of the compound of Example 1, taken daily or taken in alternate periods according to the disease considered.

Of course the sulphonated compounds described above can be administered as a single active agent or in combination with other active agents of a different kind, with the same therapeutic or non therapeutic aim.

A subject of the present invention is also the sulphonated compounds described above for their use in a method for treating the human or animal body, in particular human.

As medicaments, the sulphonated compounds corresponding to general formula I as well as their addition salts with pharmaceutically acceptable acids can be incorporated in pharmaceutical compositions intended for the digestive or parenteral route.

These pharmaceutical compositions can be solid or liquid and be presented in the pharmaceutical forms commonly used in human medicine, such as for example, plain or sugar-coated tablets, gelatin capsules, granules, suppositories, injectable preparations, ointments, creams, gels; they are prepared according to the usual methods. The active ingredient or ingredients can be incorporated therein using excipients which are usually used in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting agents, dispersants or emulsifiers, preservatives.

In these compositions, the active ingredient is advantageously present in physiologically effective doses; the above-mentioned compositions contain in particular an effective dose of 500 mg or for example of 100 mg or also of 10 mg of at least one above active ingredient, according to the compound used.

A subject of the present invention is therefore also the above pharmaceutical compositions, in particular the above pharmaceutical compositions for their use in a method for treating a pathology linked to an excessive effect of TNF in particular by direct action on TNF.

A subject of the present invention is also a method for the preparation of a composition described above, characterized in that, according to methods known per se, the active ingredient or ingredients are mixed with acceptable, in particular pharmaceutically acceptable, excipients.

Just as much a subject of the present invention is a method for the preparation of an anti-TNF agent, in particular a direct anti-TNF-alpha agent, characterized in that a compound of formula I or one of its addition salts with pharmaceutically acceptable acids is utilized as an essential active constituent of said agent.

A method for treating diseases known to be linked to the overproduction of TNF-alpha, in particular chronic inflammatory diseases comprises the administration to a patient of a physiologically effective dose of at least one above active ingredient.

The preferred conditions for implementation of the uses of the sulphonated compounds of formula I described above also apply to the other subjects of the invention referred to above, in particular to the above methods.

The following examples illustrate the present application.

Figure 3:
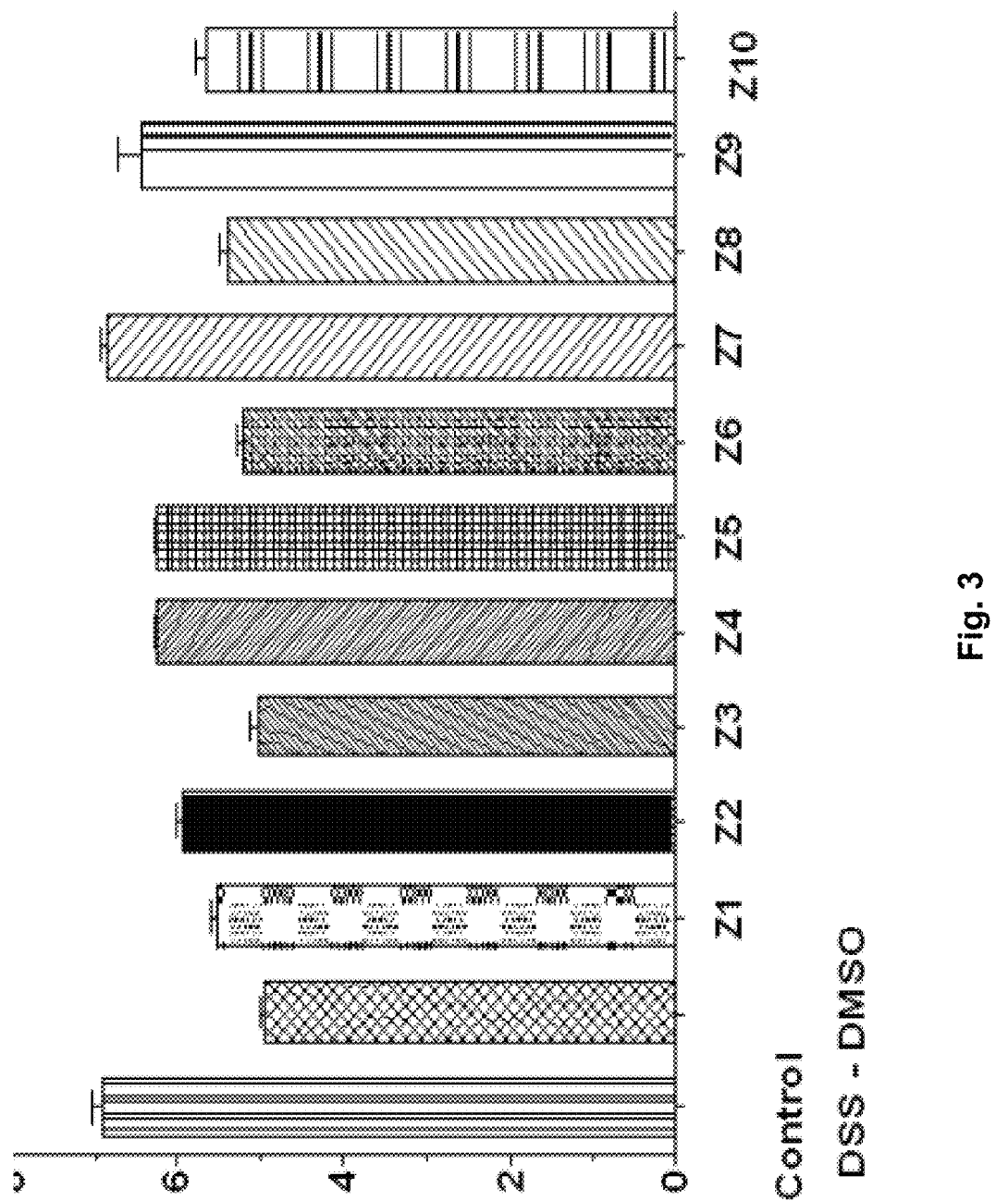

FIG. 3 present the average length (y-axis in cm) of the colons of the mice in each group after exposure to DSS. The compounds Z1 to Z10 are described below.

Figure 4:
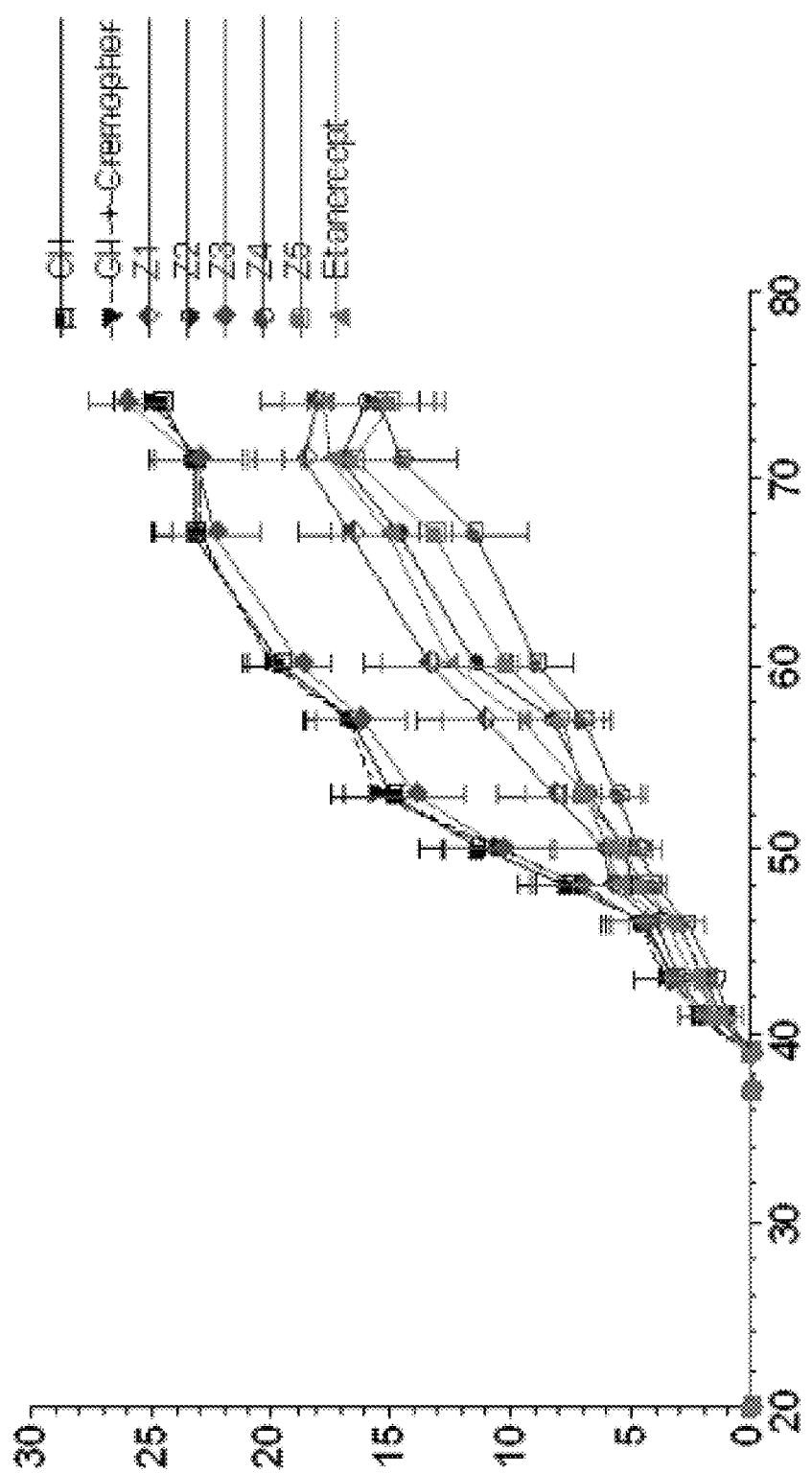

FIG. 4 shows the average clinical scores for arthritis obtained in each group with compound Z1 to Z5 as a function of the time in days (x-axis) after the last collagen injection in a model of murine collagen-induced arthritis. The control groups, Cremophor®, and etanercept are also present.

Figure 5:
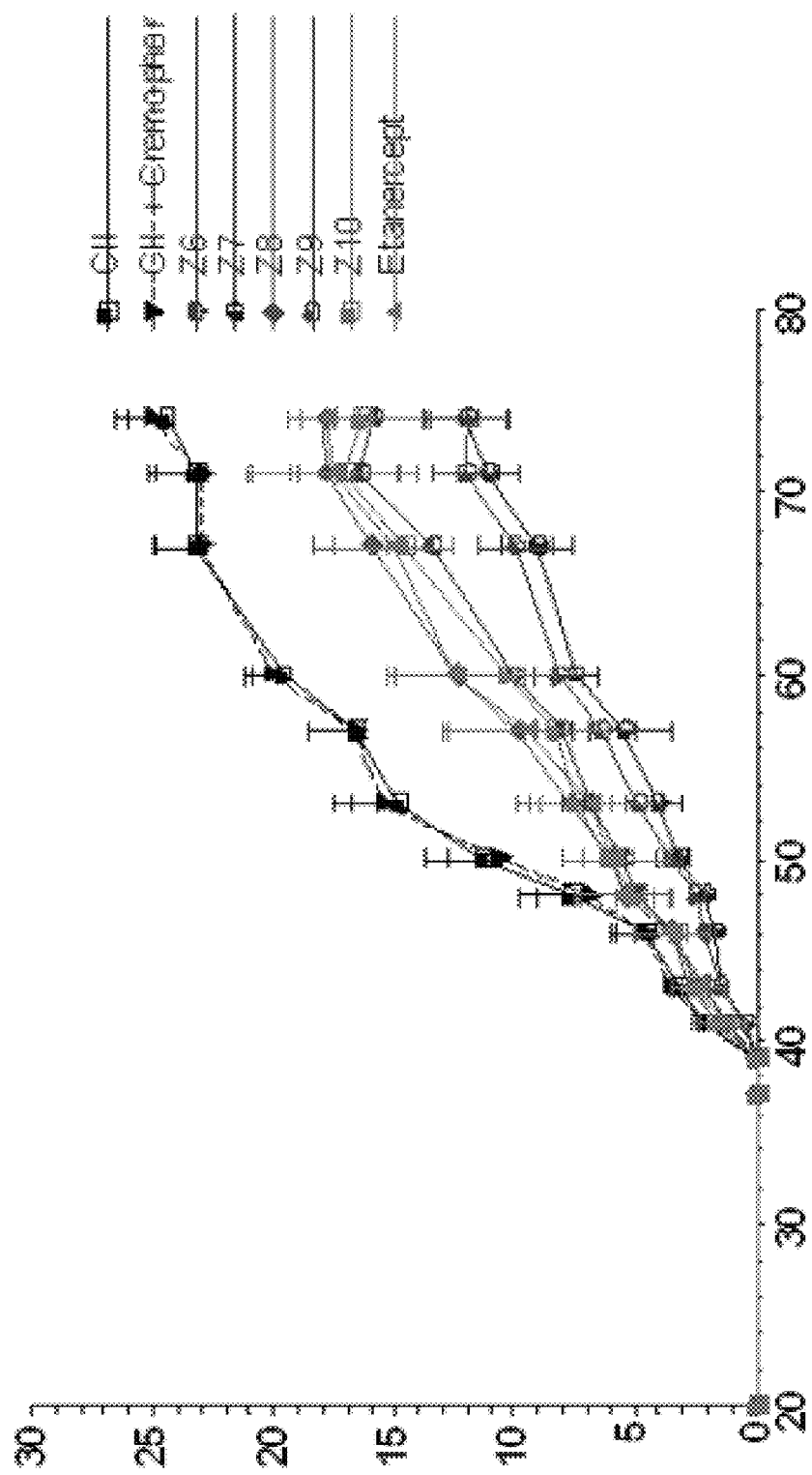

FIG. 5 shows the average clinical scores for arthritis obtained in each group with the compounds Z6 to Z10 as a function of the time in days (x-axis) after the last collagen injection, in a model of murine collagen-induced arthritis. The control groups, Cremophor®, and etanercept are also present.

Figure 6:
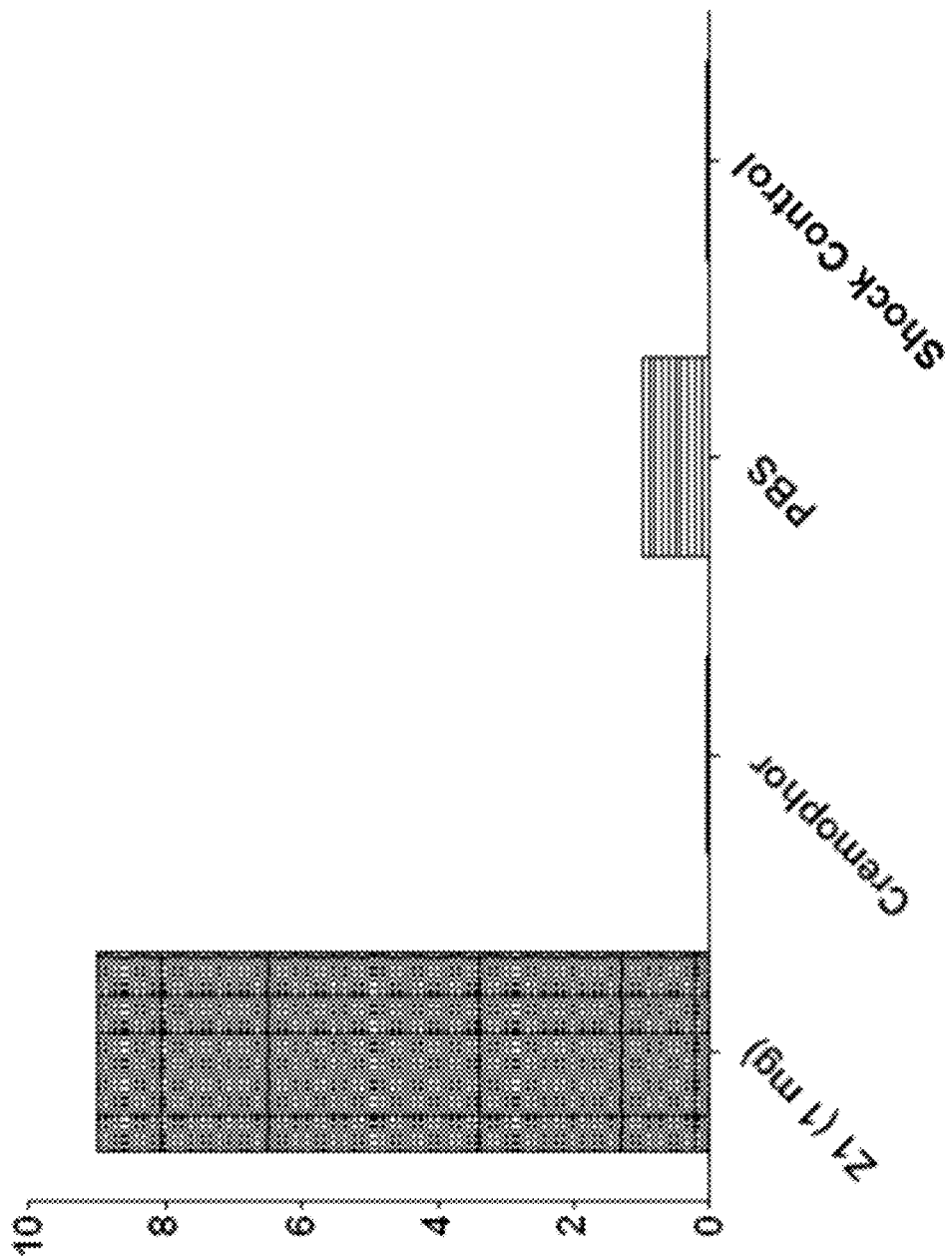

FIG. 6 shows the number of surviving mice in an endotoxin shock experiment using a murine model, following the intraperitoneal injection of compound Z1 with the controls Cremophor®, PBS, or without injection of product.

Figure 7:
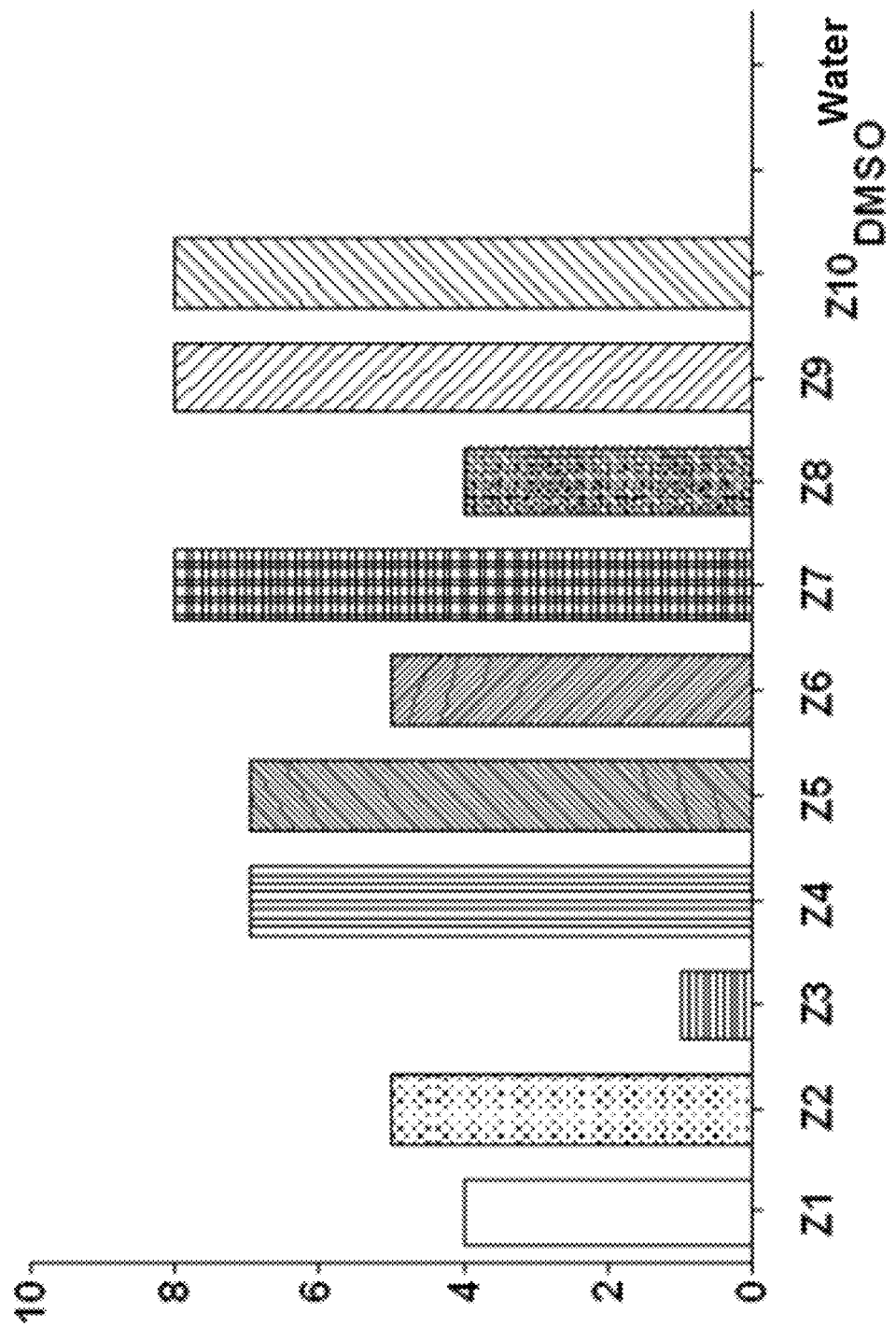

FIG. 7 shows the number of surviving mice in a murine model of endotoxin shock as a function of the product administered by oral route (Z1 to Z10). Two control groups are present with administration of DMSO or administration of water.

Figure 8:
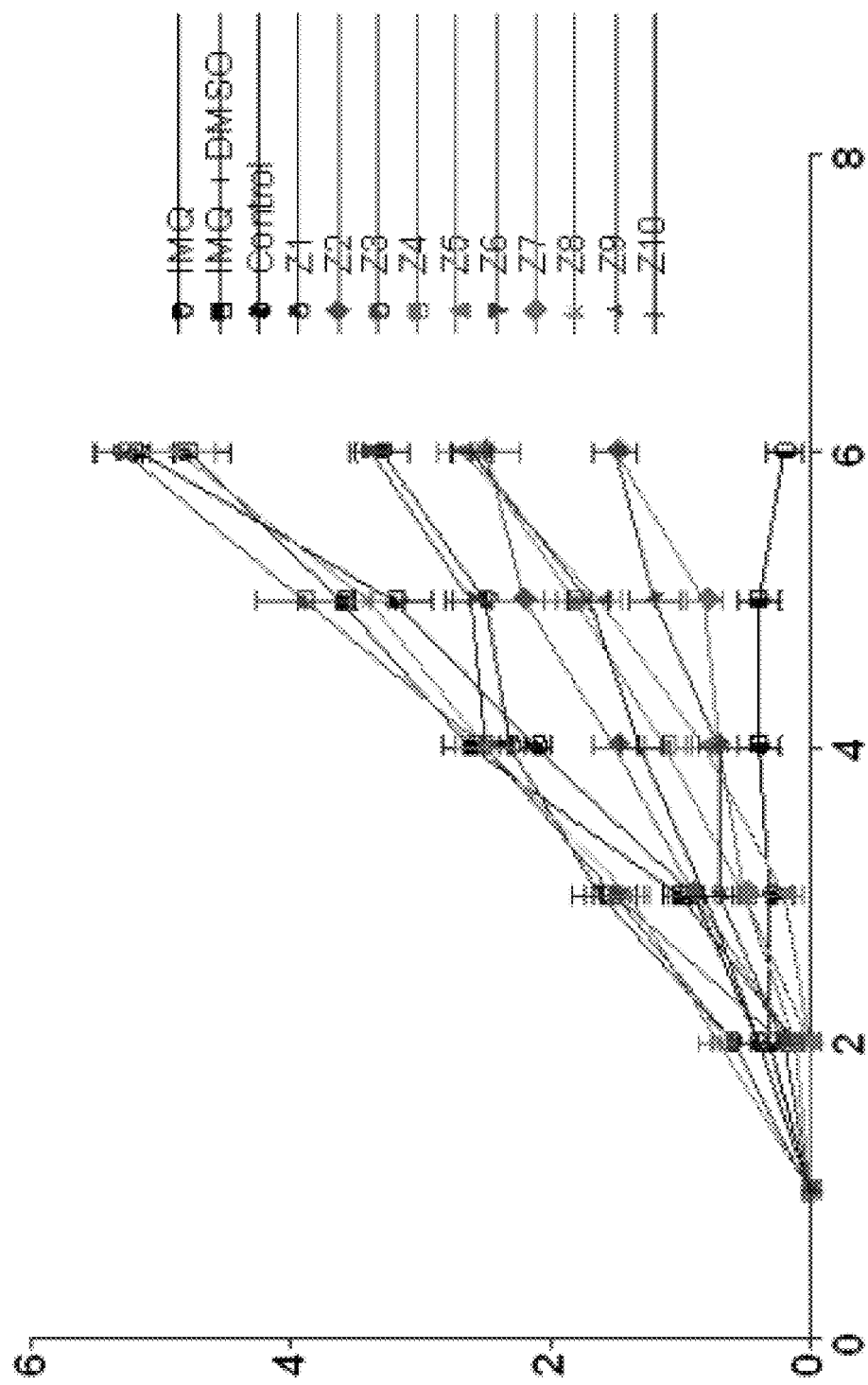

FIG. 8 shows the average overall score for each group of mice (y-axis) treated with the compounds Z1 to Z10 during the time of treatment (x-axis) with imiquimod in a psoriasis model. Three groups of controls are present: treatment with vaseline (imiquimod excipient), treatment with imiquimod alone, treatment with imiquimod and absorption of DMSO.

Figure 9:
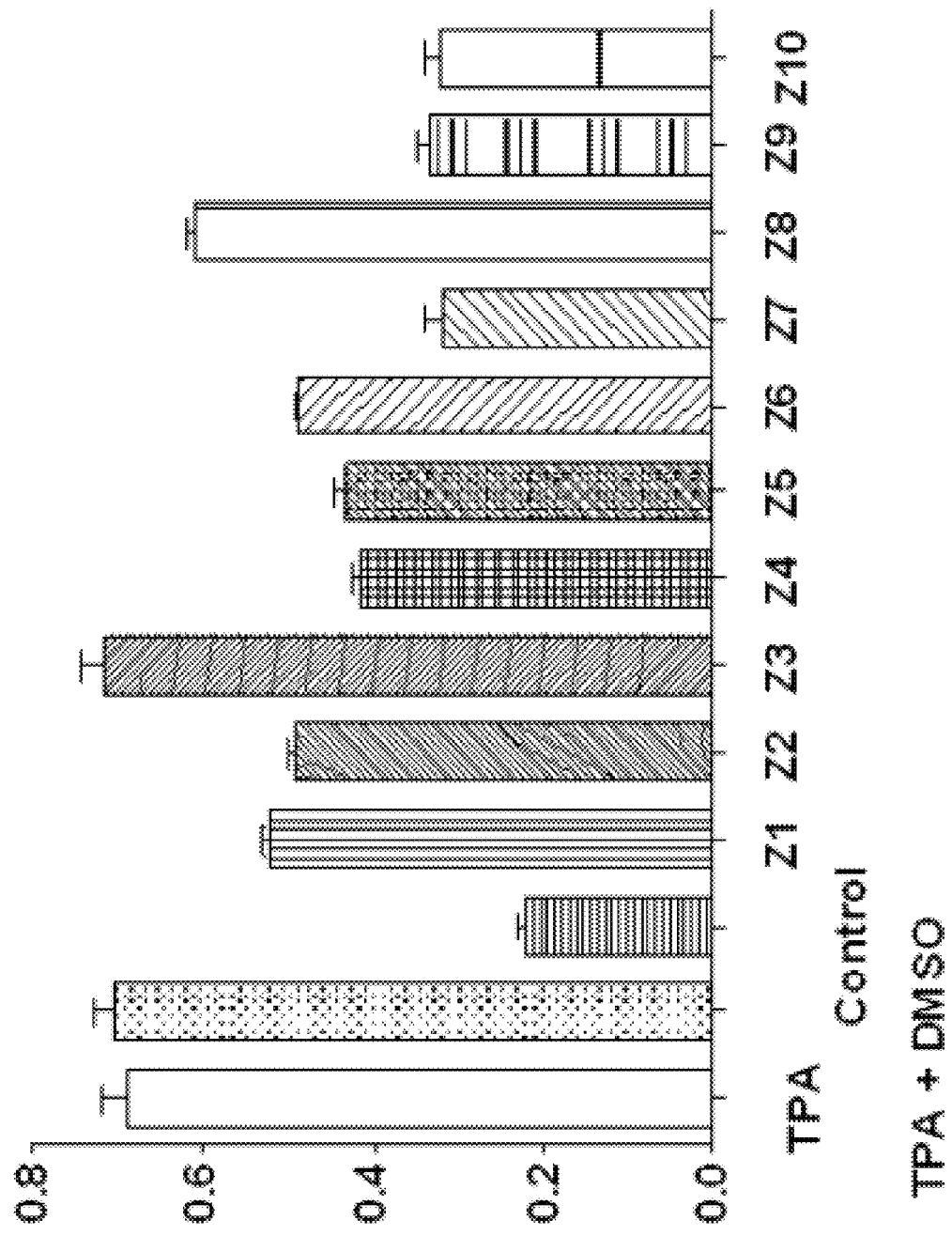

FIG. 9 shows the average size of the ears at sacrifice for each group of mice treated with compounds Z1 to Z10, following treatment of the ears with TPA. Three groups of controls are present: treatment with acetone (TPA excipient), treatment with TPA alone, treatment with TPA with absorption of DMSO.

Figure 10:
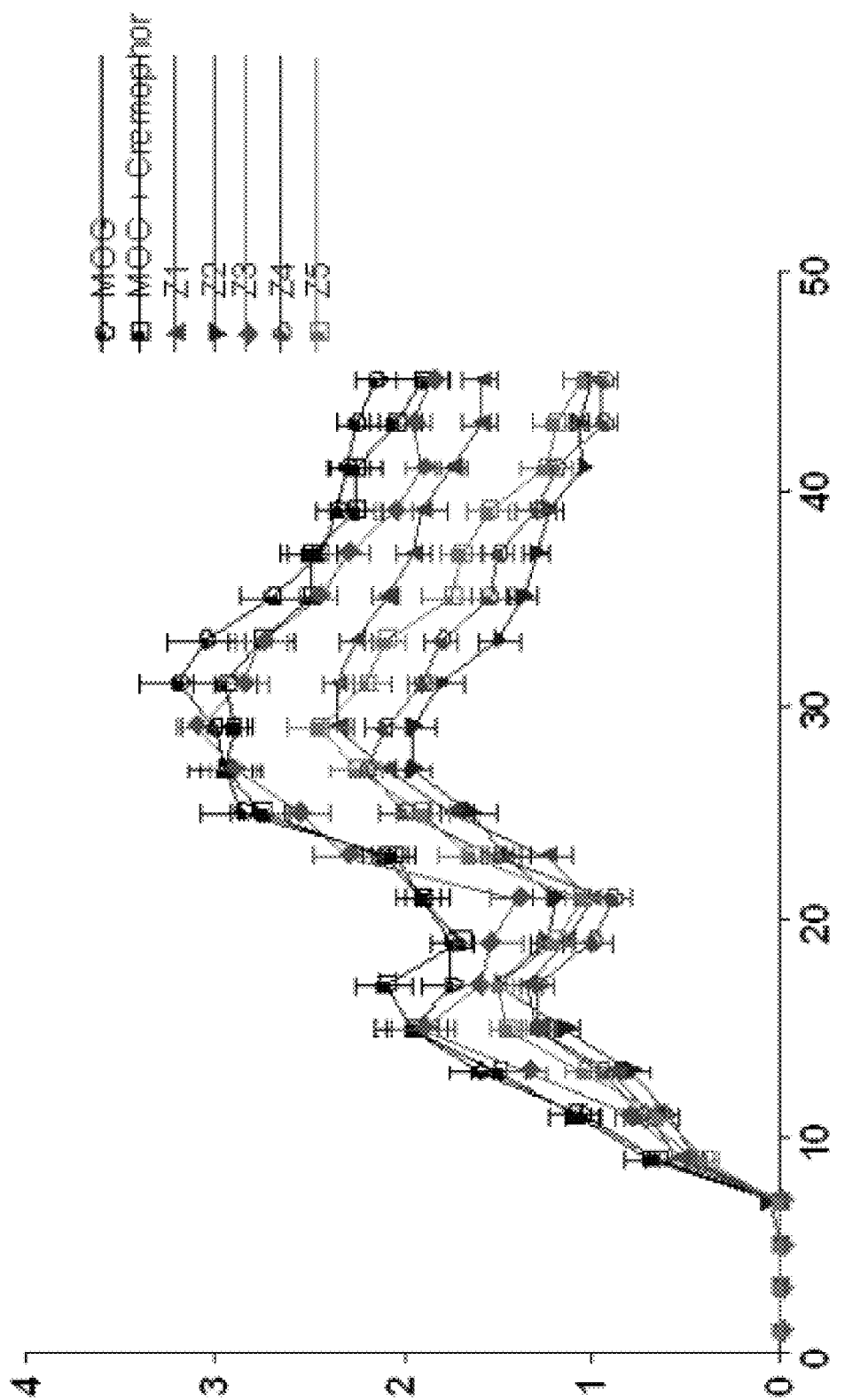

FIG. 10 shows the change in the average scores of groups of 6 mice treated with compounds Z1 to Z5, following the induction of autoimmune experimental encephalopathy, murine model of multiple sclerosis. On the x-axis, the number of days following the first injection of MOG, on the y-axis, the average paralysis score of the group of mice.

Figure 11:
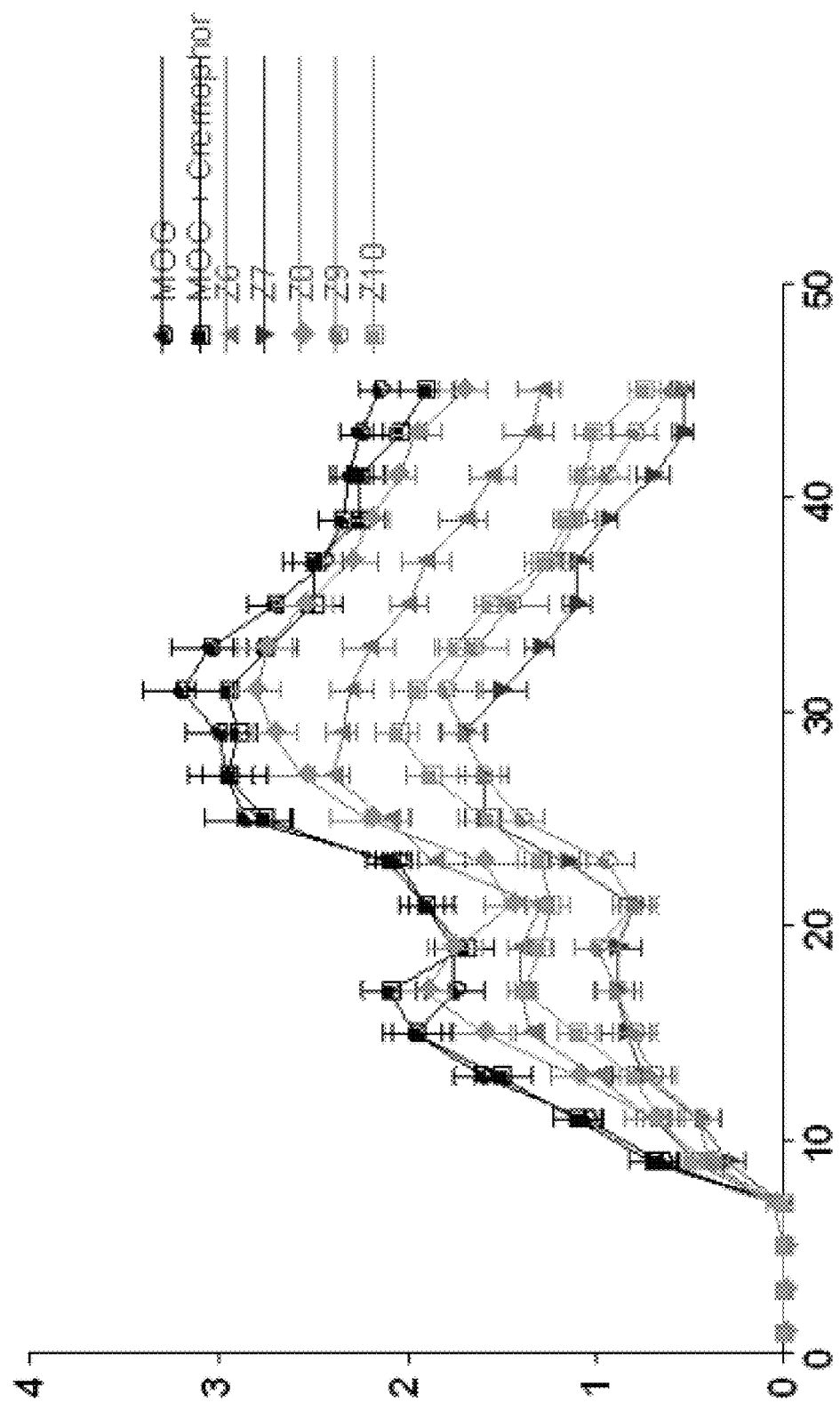

FIG. 11 shows the change in the average scores of groups of 6 mice treated with compounds Z6 to Z10, following the induction of autoimmune experimental encephalopathy, murine model of multiple sclerosis. On the x-axis, the number of days following the first injection of MOG, on the y-axis, the average paralysis score of the group of mice.

Compounds Z1 to Z10 represent respectively the compounds as identified previously in the list of compounds 1 to 36; the second number in brackets corresponds to the number of the product tested below (see tables): 1=(Z1), 3=(Z2=32), 19=(Z3=70), 13=(Z4=65), 14=(Z5=66), 15=(Z6=67), 16=(Z7=68), 18=(Z8=69), 21=(Z9=72), 22=(Z10=73).

EXAMPLE 1

Tablets corresponding to the following formula were prepared:

| | |
|---|---|
| N-(3-acetyl-2-methylnaphthho[1,2-b]furan-5-yl)-4-ethoxybenzene sulphonamide | 10 mg |
| Excipient q.s. for a tablet made up to (detail of excipient: lactose, starch, talc, magnesium stearate) | 100 mg |

EXAMPLE 2

Scored tablets corresponding to the following formula were prepared:

| | |
|---|---|
| N-(3-acetyl-2,6-dimethyl-1-benzofuran-5-yl)-4-methoxybenzene sulphonamide | 15 mg |
| Excipient q.s. for a tablet made up to (detail of excipient: lactose, starch, talc, magnesium stearate). | 100 mg |

EXAMPLE 3

Tablets corresponding to the following formula were prepared:

| | |
|---|---|
| N-[2-(4-benzyl-1-piperazinyl)-2-oxoethyl]-N-(3-chlorophenyl)-4-methyl benzenesulphonamide | 500 mg |
| Excipient q.s. for a tablet made up to (detail of excipient: lactose, starch, talc, magnesium stearate) | 100 mg |

EXAMPLE 4

Tablets corresponding to the following formula were prepared:

| | |
|---|---|
| N-benzyl-4-chloro-N-{2-[4-(2-methoxyphenyl)-1-piperazinyl]-2-oxoethyl} benzenesulphonamide | 250 mg |
| Excipient q.s. for a tablet made up to (detail of excipient: lactose, starch, talc, magnesium stearate) | 100 mg |

EXAMPLE 5

Tablets corresponding to the following formula were prepared:

| | |
|---|---|
| N-benzyl-4-bromo-N-{2-[4-(2-methoxyphenyl)-1-piperazinyl]-2-oxoethyl} benzenesulphonamide | 1 g |
| Excipient q.s. for a tablet made up to (detail of excipient: lactose, starch, talc, magnesium stearate) | 100 mg |

Experiment 1

Effects of the Sulphonated Compounds of Formula I on Human TNF-Alpha Activity The compounds are dissolved in DMSO to be used in vitro or in vivo by oral route, and in Cremophor® for their use in vivo by intraperitoneal route.

The compounds were tested for their potential to directly inhibit human TNF-alpha using a test for apoptosis induced by human TNF-alpha on murine L929 cells. The cells were cultured in DMEM medium with 10% fœtal calf serum added. $4 \times 10^4$ cells in 100 µl of culture medium were exposed to human TNF-alpha (R & D Diagnostics) at 0.150 ng/ml for 24 hours in 96-well plates, and the tested compound was added at a final concentration of 100 µM or 10 µM. A solution of MTT dye was added (100 µl at 0.5 mg/ml) to each well over two hours in order to measure cell survival. The absorbance was measured at 570 nm using a BMG Fluostar microplate reader. The inhibitory activity of the products was expressed as a calculated % survival based on the control cells without the addition of TNF. The inhibitory activity of the compounds is expressed as a % survival at 10 µM and inhibitory concentration 50 (IC50). The table below summarizes the results obtained for the sulphonated compounds of formula I tested as described above.

Figure 1:
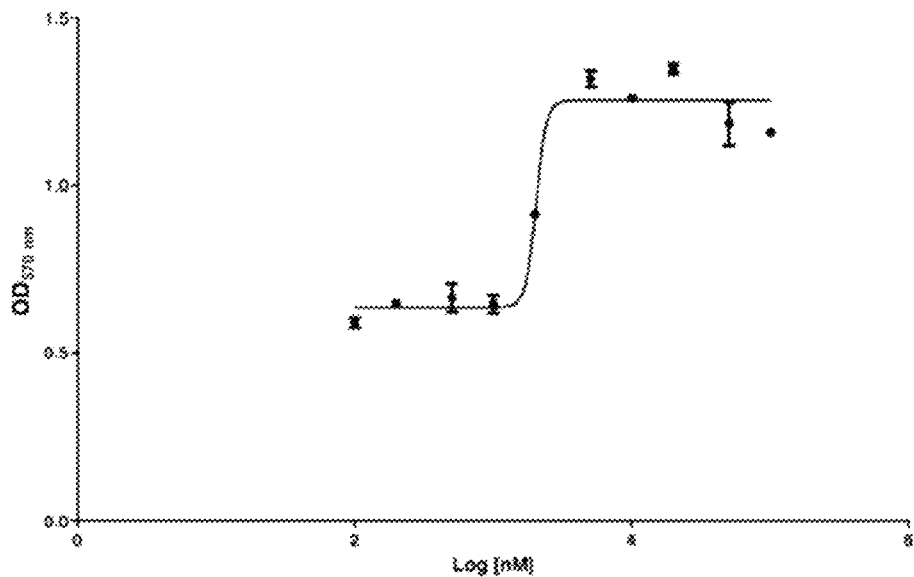
FIG. 1 shows the inhibition curve obtained by compound Z1 on the apoptogenic activity of human TNF-alpha at a concentration of 0.150 ng/ml on the line L929 (OD measured at 570 nm) as a function of the log of the concentration of compound 6.

The compounds exhibiting greater than 50% effectiveness as inhibitors of human TNF-alpha at 100 µM and 10 µM were also tested over a concentration range from 0.01 µM to 100 µM: FIG. 1 shows the inhibition curve obtained for compound 6.

The compound numbers in brackets refer to the numbers of the preferred compounds mentioned in the general part of the description.

For the sulphonated compounds below, R2=H:

| Compound | Position of the X or Xs on the benzene sulphonamide ring 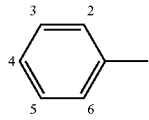 | R1 = 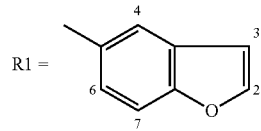 | % Inhibition 10 μM |
|---|---|---|---|
| 1 | 4-O—CH₃ | 2-CH₃; 3-CO—CH₃; 6-CH₃ | 71.15 |
| 2 | 4-O—CH₃ | 2-CH₃; 3-CO—O—CH₃ | 57.51 |
| 3 | 4-CH₃ | 2-CH₃; 3-CO—O—CH₃ | 48.09 |
| 4 | 4-O—CH₃ | 2-CH₃; 3-CO—O—CH₂—CH₃ | 41.55 |
| 5 | 4-O—CH₂—CH₃ | 2-CH₃; 3-CO—O—CH₂—CH₃ | 39.09 |
| 6 | 4-O—CH₂—CH₃ | 2-CH₃; 3-CO—O—CH₃ | 23.91 |
| 7 | 4-O—CH₂—CH₃ | 2-CH₃; 3-CO—O—CH₂—CH₃; 7-Br | 21.80 |
| 8 | 4-O—CH₂—CH₃ | 2-CH₃; 3-CO—O—CH₂—CH₃; 7-Cl | 18.36 |
| 9 | 4-CH(CH₃)₃ | 2-CH₃; 3-CO—O—CH₃ | 17.93 |
| 10 | 4-Cl; 3-CH₃ | 2-CH₃; 3-CO—O—CH₃ | 16.15 |
| 11 | 4-CH₃; 3-NO₂ | 2-CH₃; 3-CO—CH₃ | 13.57 |
| 12 | 4-O—CH₃ | 2-CH₃; 3-CO—OH | 13.31 |
| 13 | 2-CH₃; 5-CH₃ | 2-CH₃; 3-CO—O—CH₃ | 12.41 |
| 14 | 4-Cl | 2-CH₂—O—CH₃; 3-CO—O—CH₃ | 11.26 |
| 15 | 4-Cl; 3-NO₂ | 2-CH₃; 3-CO—O—CH₃ | 10.6 |
| | | R1 = 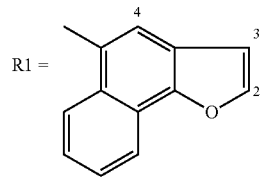 | |
| 16 (1) | 4-O—CH₂—CH₃ | 2-CH₃; 3-CO—CH₃ | 80.40 |
| 17 | 3-NO₂ | 2-CH₃; 3-CO—O—CH₂—CH₃ | 14.93 |
| 18 | 4-CH₃ | 2-CH₃; 3-CO—CH₃ | 13.61 |
| 19 | H | 2-CH₃; 3-CO—CH₃ | 6.64 |
| 20 | 4-Cl | 2-CH₃; 3-CO—CH₃ | 5.12 |
| 21 | 4-O—CH₃ | R1 = 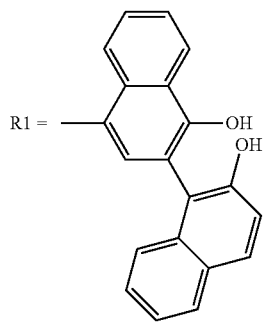 | 53.45 |
| 22 | H | R1 = 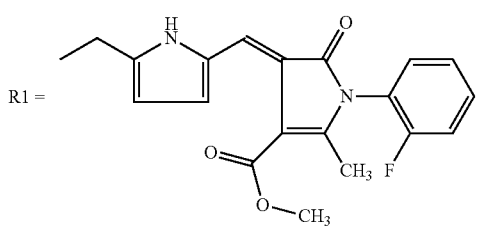 | 57.84 |

-continued

| # | Substituent | R1 structure | Value |
|---|---|---|---|
| 23 | 2-CH₃, 5-(4-benzylamino-1-methylphthalazinyl) | R1 = 2-(tetrahydrofuranyl)ethyl | 44.74 |
| 24 | 4-CH₃ | R1 = butanoate ester of 3-(4-fluorophenyl)-4-oxo-4H-chromen-7-yl | 50.26 |
| 26 | 2-CH₃, 4-CH₃, 6-CH₃ | R1 = acenaphthyl | 43.84 |
| 27 | 4-(2-oxo-acenaphthylen-1-ylamino)acetyl | R1 = 2,4-dimethoxyphenyl | 37.26 |
| 28 | 4-(4-methoxyphenylsulfonylamino) | R1 = 4-methoxyphenyl | 35.69 |
| 29 | 4-[N-(3,4-dimethoxyphenethyl)butanamido] | R1 = isobutyl (CH(CH₃)CH₃) | 34.81 |
| 30 | 3-[3-(N-benzylsulfamoyl)benzoyl] | R1 = benzyl | 31.4 |
| 31 | 4-O-CH₃ | R1 = (7-methyl-1-oxo-2,3-dihydro-1H-dibenzofuran-8-yl)methyl | 30.65 |

For the sulphonated compounds below,
R1=a —CR4-CO-R3 group where R4=H:

| Compound | Position of the X or Xs on the benzene sulphonamide ring | R2 | R3 | % Inhibition 10 μM |
|---|---|---|---|---|
| 32 (3) | 3-CH₃<br>4-O—CH₃ | 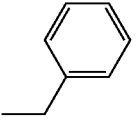 | 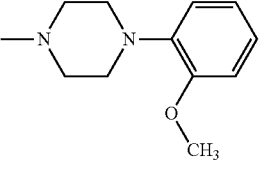 | 69.73 |
| 33 | 4-CH₃ | 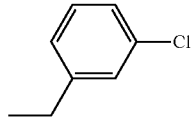 | 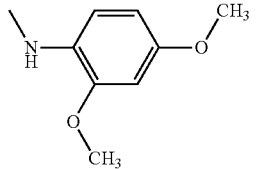 | 52.4 |
| 34 | 4-CH₃ | 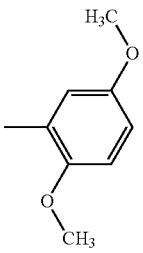 | 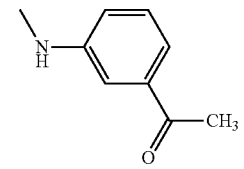 | 42.26 |
| 35 | 2-O—CH₃<br>5-CH₃ | 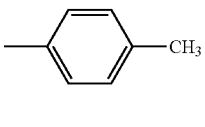 | 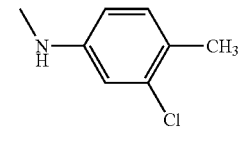 | 41.57 |
| 36 | — | 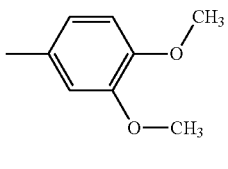 | 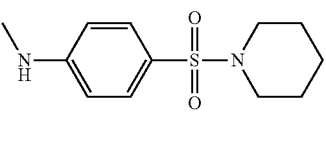 | 38.8 |
| 37 | 3-O—CH₃<br>4-O—CH₃ | 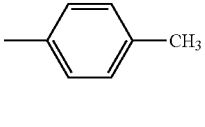 | 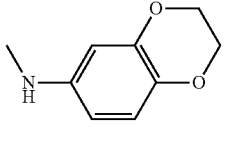 | 38.55 |
| 38 | H | 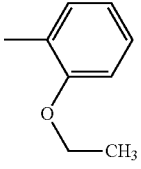 | 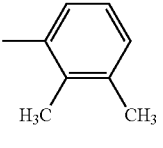 | 36.43 |
| 39 | 4-CH₃ | 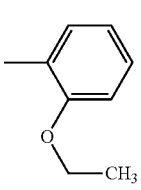 | 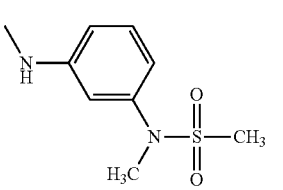 | 33.91 |

-continued

| Compound | Position of the X or Xs on the benzene sulphonamide ring | R2 | R3 | % Inhibition 10 μM |
|---|---|---|---|---|
| 40 | 3-CH₃<br>4-O—CH₃ | ethylbenzene | 4-phenylpiperazin-1-yl | 33.48 |
| 41 | 4-CH₃ | phenylpropyl (–CH₂–CH₂–C₆H₅) | m-toluidino (–NH–C₆H₄–CH₃) | 32.90 |
| 42 | 3-O—CH₃<br>4-O—CH₃ | 2,5-dimethoxy-4-methylphenyl | 2,6-diethylanilino | 31.84 |
| 43 | H | 4-bromobenzyl | benzo[d][1,3]dioxol-5-ylamino | 29.38 |
| 44 | 4-CH₃ | 3-methoxyphenyl | methyl 3-(methylamino)-4-methylbenzoate | 26.77 |
| 45 | H | 2,3-dihydro-1,4-benzodioxin-6-yl | (1,5-dimethyl-3-oxo-2-phenyl-2,3-dihydro-1H-pyrazol-4-yl)amino | 25.67 |
| 46 | 3-O—CH₃<br>4-O—CH₃ | p-tolyl | 2-(isobutylcarbamoyl)anilino | 25.60 |

-continued

| Compound | Position of the X or Xs on the benzene sulphonamide ring | R2 | R3 | % Inhibition 10 μM |
|---|---|---|---|---|
| 47 | 4-F | benzyl | 4-phenylpiperazin-1-yl methyl | 24.12 |
| 48 | 4-CH₃ | 2,3-dimethylphenyl | N-(3-(N-methyl-methylsulfonamido)phenyl)amino | 23.69 |
| 49 | 4-Cl | 2-methyl-6-ethoxyphenyl | (3,4-dimethoxyphenyl)amino | 22.99 |
| 50 | 3-O—CH₃<br>4-O—CH₃ | 4-fluorophenyl | 4-(benzo[d][1,3]dioxol-5-ylmethyl)piperazin-1-yl | 22.60 |
| 51 | 3-O—CH₃<br>4-O—CH₃ | 2,5-dimethoxy-3-methylphenyl | (2,4-dimethylphenyl)amino | 22.05 |
| 52 | 3-O—CH₃<br>4-O—CH₃ | 4-chlorophenyl | (2-ethoxyphenyl)amino | 21.46 |
| 53 | 4-CH₃ | 3-nitrophenyl | methyl 2-methyl-3-aminobenzoate | 21.08 |
| 54 | 4-Br | benzyl | 4-phenylpiperazin-1-yl methyl | 20.80 |

-continued

| Compound | Position of the X or Xs on the benzene sulphonamide ring | R2 | R3 | % Inhibition 10 μM |
|---|---|---|---|---|
| 55 | 3-O—CH₃<br>4-O—CH₃ | cyclohexyl | 2-methyl-6-ethyl-anilino (—NH—) | 20.75 |
| 56 | H | 3,4-dimethoxyphenyl-methyl | ethyl 1-piperidine-4-carboxylate | 20.42 |
| 57 | 4-CH₃ | 2-methoxyphenyl-methyl | 1,2,3,4-tetrahydroisoquinolin-2-yl | 20.00 |
| 58 | H | 2-ethoxyphenyl-methyl | 2,4,6-trimethylanilino (—NH—) | 19.30 |
| 59 | 3-O—CH₃<br>4-O—CH₃ | benzyl | 4-(2-fluorophenyl)piperazin-1-yl | 18.95 |
| 60 | 4-CH₃ | 4-methylbenzyl | 2-chlorobenzylamino (—NH—CH₂—) | 18.16 |
| 61 | 4-CH₃ | 2,5-dimethoxyphenyl-methyl | 3-[N-methyl-N-(methylsulfonyl)amino]anilino | 17.60 |

-continued
| Compound | Position of the X or Xs on the benzene sulphonamide ring | R2 | R3 | % Inhibition 10 μM |
|---|---|---|---|---|
| 62 | 3-O—CH₃<br>4-O—CH₃ | 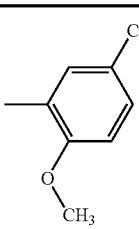 | 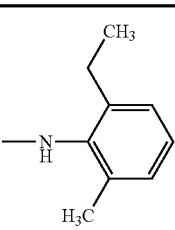 | 17.41 |
| 63 | 4-CH₃ | 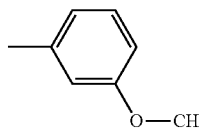 | 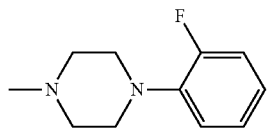 | 17.30 |
| 64 | 4-F | 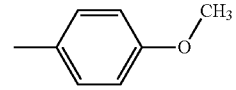 | 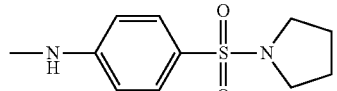 | 17.28 |
| 65 (13) | 4-CH₃ | 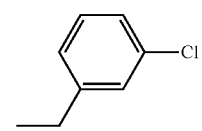 | 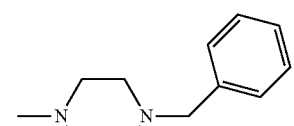 | 61.4 |
| 66 (14) | 4-Cl | 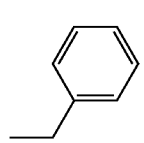 | 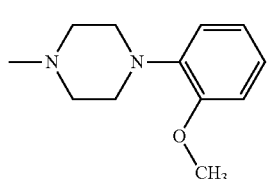 | 67.4 |
| 67 (15) | 4-Br | 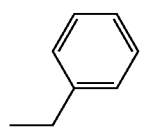 | 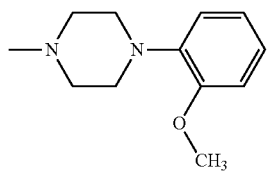 | 61.8 |
| 68 (16) | 4-CH₃ | 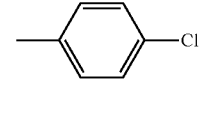 | 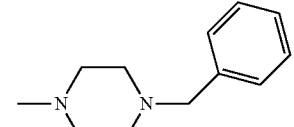 | 56.2 |
| 69 (18) | 4-CH₃ | 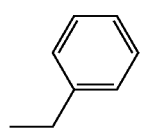 | 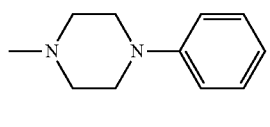 | 61.3 |

-continued

| Compound | Position of the X or Xs on the benzene sulphonamide ring | R2 | R3 | % Inhibition 10 μM |
|---|---|---|---|---|
| 70 (19) | — | 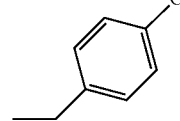 4-ethyl-methylbenzene | 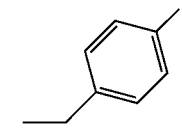 N-methylpiperazine-(2-fluorophenyl) | 54.0 |
| 71 | 4-Cl | 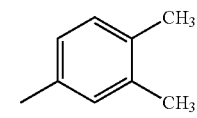 4-ethyl-fluorobenzene | N-methylpiperazine-(2-methoxyphenyl) | 53.6 |
| 72 (21) | 4-CH₃ | 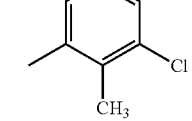 3,4-dimethyl | N-methyl-N'-benzylpiperazine | 53.4 |
| 73 (23) | — | 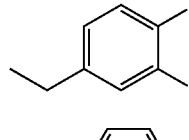 2-chloro-2,3-dimethyl | N-methyl-N'-benzylpiperazine | 44.8 |
| 74 | 4-Cl | 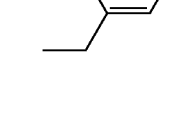 3,4-dichloro-ethylbenzene | 4-methylpiperidine | 45.6 |
| 75 | 4-F | ethylbenzene | N-methylpiperazine-(2-methoxyphenyl) | 44.7 |
| 76 | 4-CH₃ | 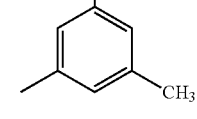 3,5-dimethyl | N-methyl-N'-benzylpiperazine | 35.5 |
| 77 | 4-O—CH₃ | ethylbenzene | 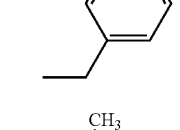 N-methylpiperazine-(2-fluorophenyl) | 32.8 |
| 78 | 3-O—CH₃ 4-O—CH₃ | 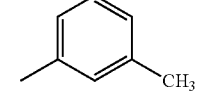 3,5-dimethyl | 2-methyl-1,2,3,4-tetrahydroisoquinoline | 38.4 |

-continued

| Compound | Position of the X or Xs on the benzene sulphonamide ring | R2 | R3 | % Inhibition 10 μM |
|---|---|---|---|---|
| 79 | 3-O—CH₃<br>4-O—CH₃ | 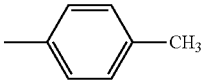 4-CH₃-phenyl | 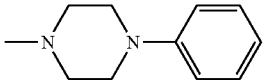 —N(piperazine)N-phenyl | 36.8 |
| 80 | — | 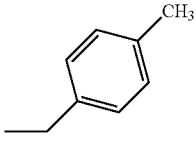 2,5-dimethyl-phenyl with ethyl | 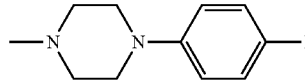 —N(piperazine)N-(4-F-phenyl) | 34.3 |
| 81 | 4-CH₃ | 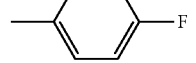 4-F-phenyl | 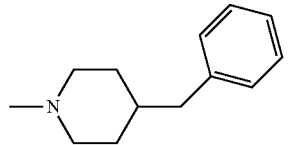 —N(piperidine)-CH₂-phenyl | 34.8 |
| 82 | 4-CH₃ | 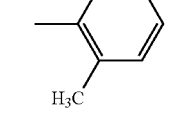 2,3-dimethyl-phenyl | 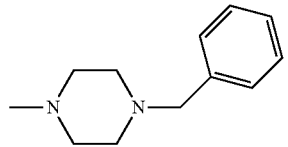 —N(piperazine)N-CH₂-phenyl | 34.6 |
| 83 | 4-CH₃ | 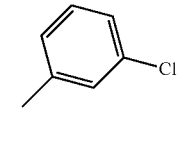 3-Cl-phenyl | 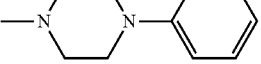 —N(piperazine)N-phenyl | 34.1 |
| 84 | 3-O—CH₃<br>4-O—CH₃ | 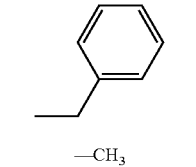 ethyl-phenyl | 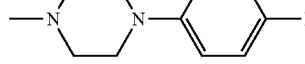 —N(piperazine)N-(4-F-phenyl) | 33.6 |
| 85 | 4-CH₃ | —CH₃ | 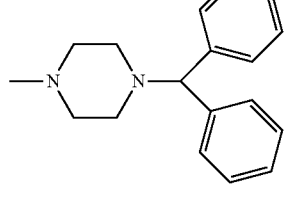 —N(piperazine)N-CH(phenyl)₂ | 32.1 |
| 86 | — | 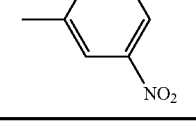 3-NO₂-phenyl-methyl | 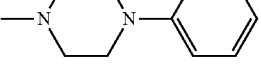 —N(piperazine)N-phenyl | 31.8 |

Experiment 2

The compounds were tested for their ability to directly inhibit murine TNF-alpha using a test for apoptosis induced on murine L929 cells by murine TNF-alpha. The cells were cultured in DMEM with 10% foetal calf serum added. $4 \times 10^4$ cells in 100 μl of culture medium in 96-well plates were exposed to murine TNF-alpha (R & D Diagnostics) at 0.3 ng/ml for 24 h, and the tested compound at a final concentration of 100 μM or 10 μM. MTT solution (100 μl at 0.5 mg/ml) was added to each well over two hours in order to measure the cell survival. The absorbance was measured at 570 nm using a BMG Fluostar microplate reader. The inhibitory activity of the medicaments was expressed as a calculated % survival based on the control cells without the addition of TNF.

The activities obtained with benzene-sulphonamide derivatives against murine TNF-alpha were similar to those obtained against human TNF-alpha.

Experiment 3

Mouse Model of Dextran Sulphate Sodium (DSS)-Induced Colitis

The benzene-sulphonamide derivatives were tested in vivo in a mouse model of DSS-induced colitis. Colitis is induced by the absorption of dextran sulphate sodium (DSS) in distilled water over the first 7 days of the test (3%). The presence of a colitis was measured by an index of the activity of the disease combining a loss of weight, rectal bleeding, diarrhoea and the presence of blood in the stools.

The DSS-induced colitis was also evaluated by macroscopic and histological analyses of the colon. Groups of 10 C57BL mice were formed. The mice in the control group received distilled water until the end of the protocol. The mice in the DSS, and DSS-DMSO groups and the mice in the DSS-BSD group received distilled water with 3% DSS for 7 days and then distilled water until the end of the protocol. During the test, from day 1 to 20 (group 1) or from day 8 to 20 (group 2) the mice received daily by oral route (po) 100 µl of phosphate buffer (PBS) (control group and DSS group), DMSO (DSS-DMSO-group), or benzene-sulphonamide derivatives at 10 mg dissolved in DMSO (DSS-BSD group). In fact, the activity of the benzene-sulphonamide derivatives on human TNF-alpha and on murine TNF-alpha are similar (see experiments 1 and 2).

At the end of the treatment, the mice were killed by cervical dislocation. The whole of the colon (including the caecum, the proximal colon and the distal colon) was excised. The colon was macroscopically assessed by determination of (a) the presence or the absence of blood and (b) the length. The presence or the absence of blood (in the caecum, the proximal colon and the distal colon) was classified as 1 or 0, respectively. The colic biopsies were histopathologically classified by an investigator (in order to assess the seriousness of the inflammation, the extent of the inflammation and damage to the digestive crypts), in a blind test.

The treatment with DSS considerably reduced the length of the colon. Even more important, the benzene-sulphonamide derivatives, administered concomitantly with the treatment with DSS (group 1), strongly inhibited the DSS-induced shortening of the colon. By contrast, the DMSO group (control excipient for the benzene-sulphonamide derivatives) had no effect on the DSS-induced shortening of the colon. Macroscopic observation revealed the constant presence of blood in the colons of the DSS mice but rarely, if ever, in the colons of the control mice. The appearance of blood was clearly less frequent (in particular in the proximal and distal colon) in the treated mice in the DSS-BSD group than in the mice in the DSS-DMSO group.

It is significant that the benzene-sulphonamide derivatives administered after the treatment with DSS had been initiated (group 2) substantially reversed the DSS-induced shortening of the colon. Even more important, the average length of the colon of the mice treated with DSS which received the benzene-sulphonamide derivatives after initiation of the treatment with DSS was not significantly different from that of the control mice which received only water. In accordance with these observations on the length of the colon, the appearance of blood was less frequent (in particular in the proximal and distal colon) in the mice treated with DSS BSD, compared with the mice treated with DSS or the mice in the DSS-DMSO group.

Figure 2:
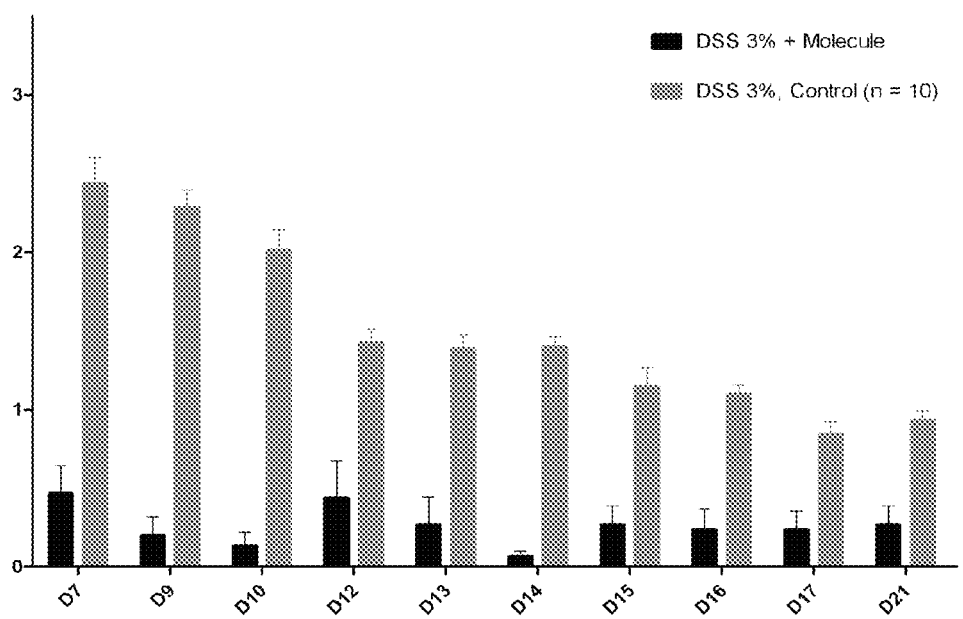
FIG. 2 shows the activity index obtained with compound Z2 as a function of the time in days after administration of DSS in a mouse model of colitis induced by DSS.

See FIGS. 2 and 3.

Experiment 4

Murine Model of Collagen-Induced Arthritis

The activity of the sulphonated compounds was tested in vivo in a murine model of collagen-induced arthritis. Collagen-induced arthritis is a well-known model of rheumatoid arthritis, which reproduces the main characteristics of the disease in humans. The experimental disease is induced in the animal by two successive injections of bovine type II collagen into the tail. The clinical signs of the disease are produced a few days later, marked mainly by serious joint inflammation and destruction of the joints. The joint inflammation can be measured and recorded in the form of clinical scores by a person skilled in the art: a score of 0 (no clinical sign) to 4 (total inflammation) is given for each joint of each mouse. Groups of 10 mice are compared based on the average value of the scores obtained on the mice. Similarly, the joint inflammation and destruction can be observed on histological sections of the joints and indicated as histological scores by a person skilled in the art.

DBA-1 mice (n=10 per treatment group) were treated two hours before the first collagen injection or received a control made up of PBS alone. Then, the mice receive twice weekly injections corresponding to a quantity of 1 mg of sulphonated compounds (diluted in Cremophor), Cremophor alone (volume of 50 µl), etanercept (10 mg/kg) until the end of the test. The clinical signs of the disease appeared concomitantly with the last collagen injection and the clinical scores gradually increased for each sick animal until day 80 (counting from the first collagen injection) when the animals were euthanized. The results show that the treatment with sulphonated compounds provides statistically significant protection in the late stage of the disease, similar to that of etanercept.

See FIGS. 4 and 5.

Experiment 5

Murine Model of Endotoxin Shock

The activity of the sulphonated compounds was tested in vivo in a murine model of endotoxin shock which is a simple conventional model of systemic inflammation induced by administration by intraperitoneal route (IP) of 0.2 µg of lipopolysaccharide (LPS) and 20 mg of D-galactosamine (GalN).

The co-administration of LPS and GalN to mice produces a lethal endotoxin shock essentially due to an overproduction of TNF-alpha. After a few hours, the mice begin to be affected and exhibit a shock syndrome. They generally die within 48 hours and the survival of the mice in each group is measured in the week following the shock. Balb/C mice (n=10 per treatment group) were treated from eight to twenty-four hours before the injection of LPS-GalN. The dose of compound injected IP into each mouse corresponds to 1 mg of the benzene-sulphonamide compound (diluted in PBS with Cremophor®) in a final volume of 50 µl). The dose administered by oral route to each mouse corresponds to 10 mg of the sulphonated compounds diluted in DMSO in a final volume of 100 µl. The results show that the treatment with the sulphonated compounds after IP administration or by oral route offers significant protection against shock similar to that provided by etanercept.

See FIGS. 6 and 7

Experiment 6

Model of Psoriasiform-Type Skin Inflammation Induced by the application of Imiquimod to the Backs of the Animals The activity of the benzene-sulphonamide compounds was tested in vivo in a model of skin inflammation by applying to the backs of the animals, shaved beforehand, a cream containing 5% Imiquimod. This product causes psoriasiform-type lesions on the skin of the animals at the application site. The mice receive 62.5 mg of cream on the back daily, which corresponds to 3.125 mg of Imiquimod per animal over 5 days. The clinical scores are evaluated on a scale of 0 to 4 relating to erythema, desquamation and the thickness of the skin on the back. The accumulated clinical scores for these three parameters make it possible to determine the severity of the inflammation with a score ranging from 0 to 12. Histological sections of the skin on the back are produced and analyzed by a person skilled in the art.

Balb/C mice (n=8 per treatment group) are shaved on the back and treated with 62.5 mg of cream containing 5% Imiquimod (i.e. 3.125 mg of imiquimod per animal). The cream is applied daily for 5 days. The establishment of inflammation (evaluation of the clinical scores) is monitored daily throughout the duration of the experiment according to 3 parameters: erythema, desquamation and the thickness of the skin of the back. During the 6 days of the experiment groups of 8 mice receive 5 mg of benzene-sulphonamide compounds in 50 µL of DMSO by oral route, one group receiving DMSO alone. The results show that benzene-sulphonamide compounds provide significant protection against psoriasiform-type skin inflammation.

See FIG. 8

Experiment 7

Model of Skin Inflammation Induced by Application of 12-O-tetradecanoylphorbol-13-acetate (TPA) to the Animals' Ears The activity of the benzene-sulphonamide compounds was tested in vivo in a model of skin inflammation by administering TPA diluted in acetone to the animals' ears. TPA is a product which causes lesions characterized by erythema and œdema on the animals' ears, similar to dermatitis. The lesions are induced by brushing the ears of Balb/C mice with 20 µL of a solution of acetone containing 0.01% TPA, the other ear being brushed with 20 µL of a solution of acetone and serving as a control. The mice receive TPA every 2 days for 10 days and the thickness of the ears is measured throughout the duration of the experiment. When sacrificed, the myeloperoxydase activity (measuring neutrophil infiltration) is determined and histological sections of the ears are produced. Balb/C mice (n=8 per treatment group) are treated with a 0.01% TPA solution of acetone on one ear and receive a solution of acetone on the other ear every two days for 10 days. The animals also receive 5 mg of benzene-sulphonamide compounds in 50 µL of DMSO per os every day for the duration of the experiment, or DMSO alone. The thickness of the ears is determined every day. The results show that the benzene-sulphonamide compounds reduce the inflammatory response. They cause a reduction in the thickness of the animals' ears as well as a reduction in the myeloperoxidase activity and cell infiltrates in the treated animals' ears.

See FIG. 9

Experiment 8

Model of Experimental Auto-Immune Encephalitis (EAE)

The activity of the benzene-sulphonamide compounds was tested in vivo in a model of experimental auto-immune encephalitis (EAE). EAE is a known model of multiple sclerosis which reproduces the main characteristics of the disease in humans. The disease is induced in animals by two successive immunizations (DO and D14) against a Myelin Oligodendrocyte Glycoprotein (MOG) polypeptide as well as by two injections of pertussis toxin (D0 and D2). The clinical signs appear few days after the second injection of MOG and are marked by neurological damage causing paralysis of the animal's limbs. Clinical monitoring is carried out daily by a person skilled in the art and the advance of the disease is evaluated by scores ranging from 0 (no clinical sign) to 5 where the animal is paralyzed in all four limbs and moribund. An average score per group is thus calculated every two days. C57BL/6 mice (n=6 per treatment group) were treated from D14 with benzene-sulphonamide compounds. They thus receive a quantity of 1 mg per mouse of benzene-sulphonamide compounds by intraperitoneal route (diluted with Cremophor) twice weekly until the end of the experiment (D45). The establishment of the disease is monitored daily by evaluation of the clinical scores from D0 (day of the first injection of MOG) to D45 (day of sacrifice of the animals). The results show that the benzene-sulphonamide compounds protect the animals from experimental auto-immune encephalitis See FIGS. 10 and 11.

The invention claimed is:

1. A method for inactivating TNF-alpha to treat a non-cancer pathology linked to an excessive effect of TNF-alpha, comprising administering to a patient in need thereof:
(i) a sulphonated compound of formula I

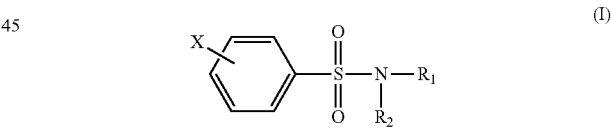

(I)

in which
• R1 represents
Φ a —CHR4-CO—R3 group, in which
R4 represents a hydrogen atom or a C1-C5 alkyl and
R3 represents an organic group, said organic group comprising 11 or more than H and containing from 6 to 30 carbon atoms including one or more rings or heterocycles, saturated or unsaturated, fused or not, unsubstituted or substituted by one or more substituents chosen from the C1-C5 alkyl, C1-C5 alkenyl, halo, C3-C8 cycloalkyl, C1-C5 alkoxy, C1-C5 alkylthio, C1-C5 alkylsulphonyl, acyl, hydroxy, NH2, nitro, C1-C5 alkylamino, di(C1-C5 alkyl)amino, acylamino radicals, said organic group not being linked to the carboxyl by a —NH—CH2— group or by a —NH—CH-alk-group where alk represent an alkyl radical with 1 to 5 carbon atoms, said organic group not comprising a

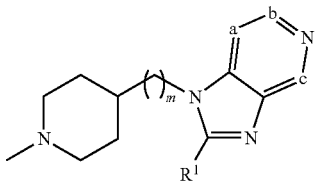

group in which m represents 0, 1 or 2, a, b and c represent CR, where each R represents independently a hydrogen or a C1-C4 alkyl, R1 represents a C1-C4 alkyl or a C3-C7 cycloalkyl, said organic group not comprising a —CO—NHOH group, said organic group not representing a

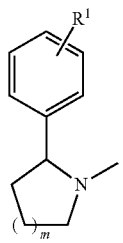

group in which n=1 or 2 and R1 represents H, halogen, CN, lower alkyl or alkoxy, optionally substituted by a halogen, Φ a benzofuran group, unsubstituted or substituted by one or more substituents chosen from the C1-C5 alkyl, C1-C5 alkenyl, halo, C3-C8 cycloalkyl, C1-C5 alkoxy, C1-C5 alkylthio, C1-C5 alkylsulphonyl, acyl, hydroxy, NH2, nitro, C1-C6 alkylamino, di(C1-C6 alkyl)amino, acylamino radicals, Φ a hydrogen atom, Φ a group chosen from a¶
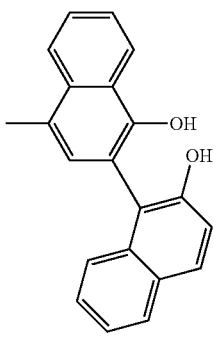

b¶
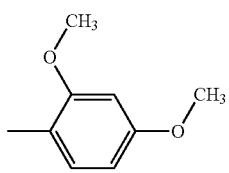

c¶
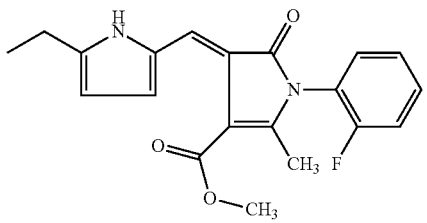

d¶
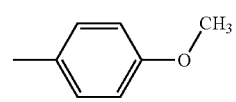

e¶
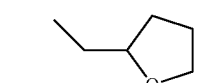

f¶
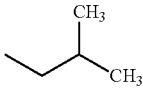

g¶
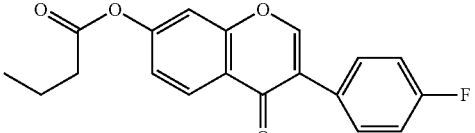

h¶
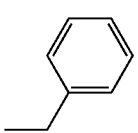

i¶
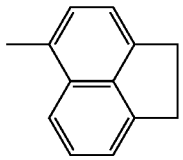

j¶
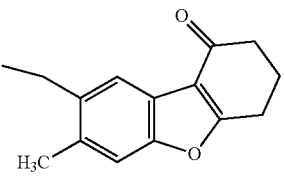

- R2 represents
  Φ a phenyl or C4-C7 cycloalkyl group unsubstituted or substituted by one or more substituents chosen from the C1-C5 alkyl, C1-C5 alkenyl, halo, C3-C8 cycloalkyl, C1-C5 alkoxy, C1-C5 alkylthio, C1-C5 alkylsulphonyl, acyl radicals except for —CO NHOH, hydroxy, NH2, nitro, C1-C6 alkylamino, di(C1-C6 alkyl)amino radicals; two substituents in meta position relative to one another being able to form a ring, said group being directly linked to the nitrogen, or linked by a —(CH$_2$)$_n$— group where n=1, 2 or 3,
  Φ a hydrogen atom,
  it being understood that R1 and R2 cannot at the same time represent hydrogen,
- X represents a hydrogen atom or one or more substituents chosen from the C1-C5 alkyl, C1-C5 alkoxy, C1-C5 alkenyl, halo, C3-C8 cycloalkyl, C1-C5 alkylthio, C1-C5 alkylsulphonyl, acyl, hydroxy, NH2, nitro, C1-C6 alkylamino, di(C1-C6 alkyl)amino, acylamino radicals, it being understood that X is not a 3,4-dialkoxy or a 3,4-dialkylthio, with the proviso that the sulphonated compound of formula I is not N—[2-(4-benzyl-1-piperazinyl)-2-oxo-ethyl]—N—(3,4-dimethylphenyl)-4-methylbenzenesulphonamide;

(ii) a compound of formula I below for which R2=H:
the compound for which

X = 2-methyl and 5- 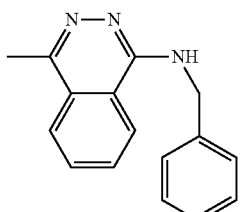 and R1 = 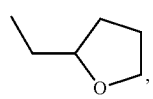, the compound for which

X = 4- 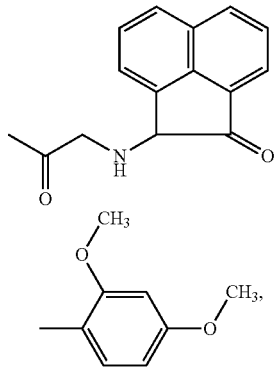 and R1 = 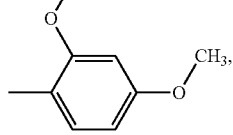, the compound for which

X = 4- 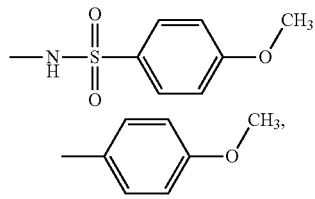 and R1 = 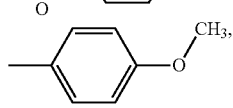, the compound for which

X = 4- 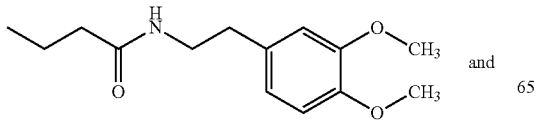 and

R1 = 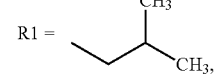

the compound for which

X = 3- 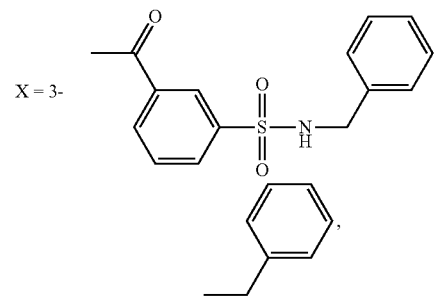 and R1 = , or
(iii) 3-(3-phenoxyphenyl)-2-(phenylsulphonyl)—N—(3-pyridinylmethyl) acrylamide,
or an addition salt of (i), (ii) or (iii) with pharmaceutically acceptable acid it being understood that
  if R1=H and X is a 3-nitro,4-chloro, R2 is not a benzyl radical,
  if R1=H, R2 is not a 3,4-dimethoxy phenethyl,
  if R1=H and X=H or alkyl optionally substituted at position 4, R2 is not an optionally substituted phenyl radical.

2. The method of claim 1, wherein the non-cancer pathology linked to an excessive effect of TNF-alpha is selected from the group consisting of an inflammatory disease of the intestine, inflammation, chronic inflammatory diseases, rheumatoid arthritis, juvenile rheumatoid arthritis, psoriatic arthritis, arthrosis, refractory rheumatoid arthritis, non-rheumatoid chronic arthritis, bone resorption/osteoporosis, Crohn's disease, haemorrhagic rectocolitis, septic shock, endotoxin shock, atherosclerosis, ischaemia-reperfusion lesions, coronary heart disease, vasculitis, amydoloidosis, multiple sclerosis, septicaemia, chronic recurrent uveitis, hepatitis C virus, malaria, ulcerative colitis, cachexia, psoriasis, endometriosis, Behçet's disease, Wegener's granulomatosis, meningitis, AIDS, HIV infections, auto-immune diseases, immunodeficiency, common variable immunodeficiency (CVID), chronic graft-versus-host diseases, trauma and graft rejections, respiratory distress syndrome, pulmonary fibrosis, diabetes, juvenile diabetes, ankylosing spondylitis, and skin disorders due to delayed-type hypersensitivity reactions, Alzheimer's disease, disseminated lupus erythematosus, and allergic asthma, and an inflammatory diseases for which the anti-TNF biotherapies (monoclonal antibodies, soluble receptors) are effective.

3. The method of claim 1, wherein, in the sulphonated compound,
R1 represents a —CHR4-CO—R3 group, in which
  R4 represents a hydrogen atom or a C1-C5 alkyl and
  R3 has the meanings already indicated in claims 1 and
  R2 and X have the meaning already indicated in claim 1,
  or one of its addition salts with pharmaceutically acceptable acids.

4. The method of claim 1, wherein, in the sulphonated compound,

R1 represents a —CHR4-CO—R3 group, in which R3 and R4 have the meaning already indicated, R2 represents an optionally substituted phenyl group, said phenyl group being directly linked to the nitrogen, or linked by a —(CH₂)— group, and X has the meaning already indicated, or one of its addition salts with pharmaceutically acceptable acids.

5. The method of claim 1, wherein, in the sulphonated compound,

R1 represents a —CHR4-CO—R3 group, in which

R4 represents a hydrogen atom or a C1-C5 alkyl and

R3 represents a

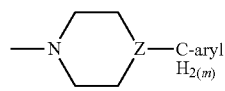

group in which m has the value 0, 1 or 2, Z has the meaning N or CH, and Ar represents an optionally substituted aryl radical, R2 represents an optionally substituted phenyl group, said phenyl group being directly linked to the nitrogen, or linked by a —(CH₂)— group, and X has the meaning already indicated, or one of its addition salts with pharmaceutically acceptable acids.

6. The method of claim 1, wherein, in the sulphonated compound,

R1 represents a —CHR4-CO—R3 group in which

R4 represents a hydrogen atom or a C1-C5 alkyl and

R3 represents a

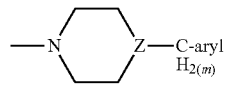

group in which m has the value 0, 1 or 2, Z has the meaning N or CH, and Ar represents an optionally substituted aryl radical, and R2 and X have the meaning already indicated, or one of its addition salts with pharmaceutically acceptable acids.

7. The method of claim 1, wherein, in the sulphonated compound,

R1 represents an optionally substituted benzofuran or naphthofuran group

R2=H and

X has the meaning already indicated, or one of its addition salts with pharmaceutically acceptable acids.

8. The method of claim 1, wherein the compound administered is selected from the sulphonated compounds consisting of:

1—N-(3-acetyl-2-methylnaphthho[1,2-b]furan-5-yl)-4-ethoxybenzene sulphonamide;

2—N-(3-acetyl-2,6-dimethyl-1-benzofuran-5-yl)-4-methoxybenzene sulphonamide;

3—N-benzyl-4-methoxy-N-{2-[4-(2-methoxyphenyl)-1-piperazinyl]-2-oxoethyl}-3-methylbenzenesulphonamide;

4—methyl 1-(2-fluorophenyl)-2-methyl-5-oxo-4-[(5-{[(phenylsulphonyl)amino]methyl}-2-furyl)methylene]-4,5-dihydro-1H-pyrrole-3-carboxylate;

5—methyl 5-{[(4-methoxyphenyl)sulphonyl]amino}-2-methyl-1-benzofuran-3-carboxylate;

6—N-(1',2-dihydroxy-1.2'-binaphthhalen-4'-yl)-4-methoxybenzene-sulphonamide;

7—N-2-(3-chlorobenzyl)-N-1-(2,4-dimethoxyphenyl)-N-2-[(4-methylphenyl)sulphonyl]glycinamide;

8—3-(fluorophenyl)-4-oxo-4H-chromen-7-yl N-[(4-methylphenyl)sulphonyl]-beta-alaninate;

9—methyl 2-methyl-5-{[(4-methylphenyl)sulphonyl]amino}-1-benzofuran-3-carboxylate;

10—5-[4-(benzylamino)-1-phthalazinyl]-2-methyl-N-(tetrahydro-2-furanylmethyl)benzenesulphonamide;

11—N-(1,2-dihydro-5-acenaphthhylenyl)-2.4,6-trimethylbenzenesulphonamide;

12—N-1-(3-acetylphenyl)-N-2-(2,5-dimethoxyphenyl)-N-2-[(4-methylphenyl)sulphonyl]glycinamide; and an addition salt thereof with pharmaceutically acceptable acid.

9. The method of claim 1, wherein the compound administered is a benzene sulphonamide selected from the consisting of:

13—N-[2-(4-benzyl-1-piperazinyl)-2-oxoethyl]-N-(3-chlorophenyl)-4-methyl benzenesulphonamide;

14—N-benzyl-4-chloro-N-{2-[4-(2-methoxyphenyl)-1-piperazinyl]-2-oxoethyl}benzenesulphonamide;

15—N-benzyl-4-bromo-N-{2-[4-(2-methoxyphenyl)-1-piperazinyl]-2-oxoethyl}benzenesulphonamide;

16—N-[2-(4-benzyl-1-piperazinyl)-2-oxoethyl]-N-(4-chlorophenyl)-4-methyl benzenesulphonamide;

17—N-benzyl-4-methoxy-N-{2-[4-(2-methoxyphenyl)-1-piperazinyl]-2-oxoethyl}-3-methylbenzenesulphonamide;

18—N-benzyl-4-methyl-N-[2-oxo-2-(4-phenyl-1-piperazinyl)ethyl]benzenesulphonamide;

19—N-{2-[4-(2-fluorophenyl)-1-piperazinyl]-2-oxoethyl}-N-(4-methylbenzyl) benzenesulphonamide;

20—4-chloro-N-(4-fluorobenzyl)-N-{2-[4-(2-methoxyphenyl)-1-piperazinyl]-2-oxoethyl}benzenesulphonamide;

22—N-[2-(4-benzyl-1-piperazinyl)-2-oxoethyl]-N-(3-chloro-2-methylphenyl)benzenesulphonamide;

23—4-chloro-N-(3,4-dichlorobenzyl)-N-[2-(4-methyl-1-piperidinyl)-2-oxoethyl]benzenesulphonamide;

24—N-benzyl-4-fluoro-N-{2-[4-(2-methoxyphenyl)-1-piperazinyl]-2-oxoethyl}benzenesulphonamide;

25—N-[2-(4-benzyl-1-piperazinyl)-2-oxoethyl]-N-(3,5-dimethylphenyl)-4-methylbenzenesulphonamide;

26—N-benzyl-N-{2-[4-(2-fluorophenyl)-1-piperazinyl]-2-oxoethyl}-4-methoxybenzenesulphonamide;

27—N-[2-(3,4-dihydro-2(1H)-isoquinolinyl)-2-oxoethyl]-N-(3,5-dimethylphenyl)-3,4-dimethoxybenzenesulphonamide;

28—3,4-dimethoxy-N-(4-methylphenyl)-N-[2-oxo-2-(4-phenyl-1-piperazinyl)ethyl]benzenesulphonamide;

29—N-{2-[4-(4-fluorophenyl)-1-piperazinyl]-2-oxoethyl}-N-(4-methylbenzyl)benzenesulphonamide;

30—N-[2-(4-benzyl-1-piperidinyl)-2-oxoethyl]-N-(4-fluorophenyl)-4-methylbenzenesulphonamide;

31—N-[2-(4-benzyl-1-piperazinyl)-2-oxoethyl]-4-methyl-N-(2-methylphenyl)benzenesulphonamide;

32—N-benzyl-N-{2-[4-(4-fluorophenyl)-1-piperazinyl]-2-oxoethyl}-4-methylbenzenesulphonamide;

33—N-(3-chlorophenyl)-4-methyl-N-[2-oxo-2-(4-phenyl-1-piperazinyl)ethyl]benzenesulphonamide;

34—N-benzyl-N-{2-[4-(4-fluorophenyl)-1-piperazinyl]-2-oxoethyl}-3,4-dimethoxybenzenesulphonamide;

35—N-{2-[4-(diphenylmethyl)-1-piperazinyl]-2-oxoethyl}-N,4-dimethyl benzenesulphonamide 36—N-(3-nitrophenyl)-N-[2-oxo-2-(4-phenyl-1-piperazinyl)ethyl]benzenesulphonamide: and an addition salt thereof with pharmaceutically acceptable acid.

10. The method of claim 8, wherein th sulphonated compound administered is a benzene sulphonamide compound bearing the number 1 or 2, or one of its additional salts with pharmaceutically acceptable acids.

11. The method of claim 1, wherein the compound, or an addition salt thereof with a pharmaceutically acceptable acid, administered is an active ingredient in a pharmaceutical composition which further comprises a compound having anti-TNF-alpha properties of a different kind, or an addition salt thereof with a pharmaceutically acceptable acid, and one or more pharmaceutically acceptable excipients.

12. The method of claim 9, wherein the sulphonated compound administered is a benzene suplhonamide compound bearing the number 13, 14, 15, 16, 18, 19 or 22, or one of its addition salts with pharmaceutically acceptable acids.

13. The method of claim 12, wherein the benzene supohonamide compound is bearing the number 13, 14 and 16, or one of its addition salts with pharmaceutically acceptable acids.

* * * * *